(12) United States Patent
Zanoni et al.

(10) Patent No.: US 9,399,077 B2
(45) Date of Patent: Jul. 26, 2016

(54) METALLOCENE COMPOUNDS AND LABELED MOLECULES COMPRISING THE SAME FOR IN VIVO IMAGING

(71) Applicant: Aptenia S.r.l., Milan (IT)

(72) Inventors: Guiseppe Zanoni, Rottofreno (IT); Alessio Porta, Certosa di Pavia (IT); Marco Pazzi, Casteggio (IT); Andrea Gandini, Casteggio (IT); Wolfgang Karl-Diether Brill, Birr (CH)

(73) Assignee: Aptenia S.r.l., Milan (IT)

( * ) Notice: Subject to any disclaimer, the term of this patent is extended or adjusted under 35 U.S.C. 154(b) by 0 days.

(21) Appl. No.: 14/771,462

(22) PCT Filed: Mar. 5, 2014

(86) PCT No.: PCT/EP2014/054270
§ 371 (c)(1),
(2) Date: Aug. 28, 2015

(87) PCT Pub. No.: WO2014/135590
PCT Pub. Date: Sep. 12, 2014

(65) Prior Publication Data
US 2016/0008495 A1 Jan. 14, 2016

(30) Foreign Application Priority Data
Mar. 7, 2013 (EP) .................................... 13158111

(51) Int. Cl.
| C07K 17/00 | (2006.01) |
| A61K 51/04 | (2006.01) |
| A61K 51/08 | (2006.01) |
| A61K 49/08 | (2006.01) |
| A61K 49/14 | (2006.01) |
| C07F 17/00 | (2006.01) |

(52) U.S. Cl.
CPC .............. *A61K 51/0487* (2013.01); *A61K 49/08* (2013.01); *A61K 49/085* (2013.01); *A61K 49/14* (2013.01); *A61K 51/083* (2013.01); *A61K 51/088* (2013.01); *C07F 17/00* (2013.01)

(58) Field of Classification Search
CPC ............ A61K 51/0487; A61K 51/088; A61K 51/083; A61K 49/085; A61K 49/14; C07F 17/00
USPC .................... 530/317, 345; 556/8, 51, 55, 56; 548/404; 546/6
See application file for complete search history.

(56) References Cited

U.S. PATENT DOCUMENTS

| 2009/0005338 A1 | 1/2009 | Gansauer et al. |
| 2013/0041104 A1 | 2/2013 | Scabini |

FOREIGN PATENT DOCUMENTS

| DE | 10 2010 007 097 A1 | 8/2011 |
| DE | 10 2010 109 187 A1 | 2/2013 |
| EP | 953 580 A1 | 3/1999 |
| EP | 055 306 A1 | 10/1999 |

OTHER PUBLICATIONS

Abstract: Pazzi, Marco et al., Immobilized Reagents for the Staudinger Coupling of Tissue-Selective Agents with Imaging Tracers, Chemical Abstracts Service, XP002703145, Database Accession No. 2013:201122 (Feb. 7, 2013).
Abstract: Yanlong, Qian et al., Synthesis of (3-methoxypropyl)-cyclopentadienyltitanium and Zirconium Complexes, Polyhedron, 12(8), 967-970 (Apr. 1993).
Abstract: Causey, Patrick W. et al, Organometallics, 23, 4486-4494 (Aug. 20, 2004).

*Primary Examiner* — Porfirio Nazario Gonzalez
(74) *Attorney, Agent, or Firm* — Millikin Intellectual Property Law, PLLC

(57) ABSTRACT

The present invention concerns compounds and methods of labeling peptides or other molecules with $^{18}$F or $^{19}$F or any other suitable radionuclide of use, for example, in PET or NMR in vivo imaging. A targeting molecule such as a protein or a peptide is linked to a substituted metallocene complex which is reacted with the $^{18}$F or $^{19}$F shortly before performing the PET or NMR in vivo imaging on the patient. The labeled molecule is then used for targeting a cell, tissue, organ or pathogen to be imaged or detected.

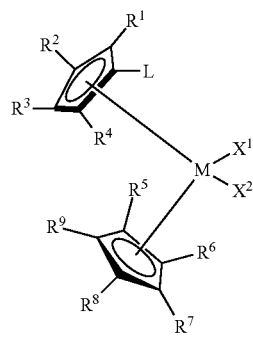

Formula I

14 Claims, 1 Drawing Sheet

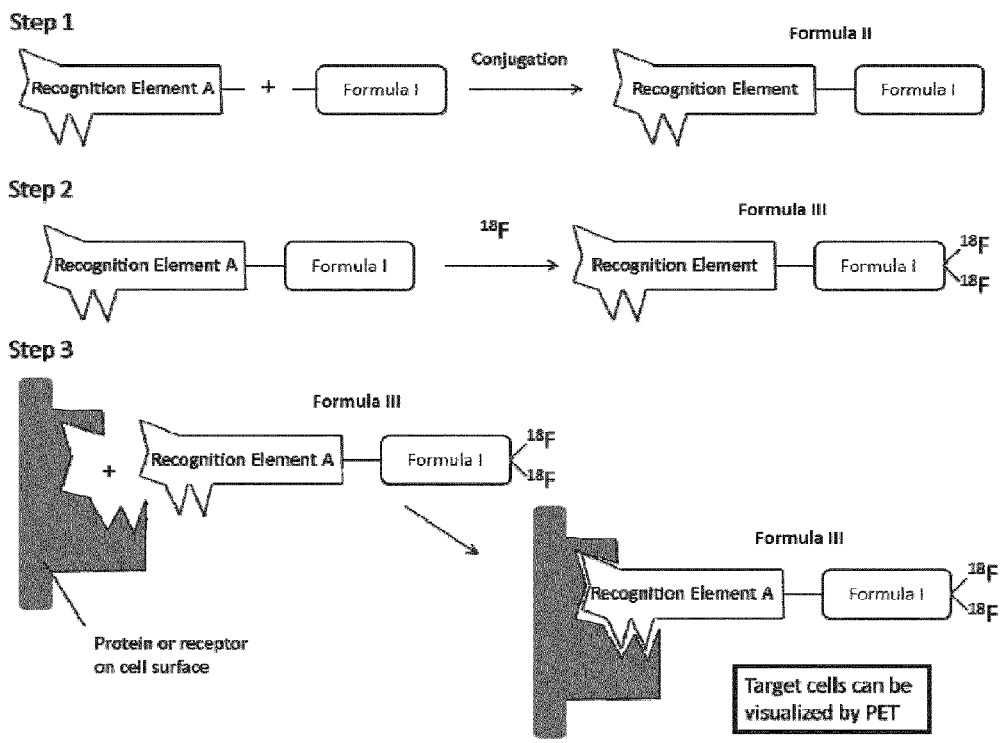

METALLOCENE COMPOUNDS AND LABELED MOLECULES COMPRISING THE SAME FOR IN VIVO IMAGING

CROSS-REFERENCE TO RELATED APPLICATIONS

This application is a continuation and national stage application of International Application No. PCT/EP2014/054270, filed Mar. 5, 2014, which claims the benefit of European Patent Application No. 13158111.8 filed on Mar. 7, 2013, the entire contents of both of which are hereby incorporated by reference.

FIELD OF THE INVENTION

The present invention concerns compounds and methods of labeling peptides or other molecules with $^{18}$F or $^{19}$F or any other suitable radionuclide of use, for example, in PET or NMR in vivo imaging. A targeting molecule such as a protein or a peptide is linked to a substituted metallocene complex which is reacted with the $^{18}$F or $^{19}$F shortly before performing the PET or NMR in vivo imaging on the patient. In certain embodiments, the labeled molecule may be used for targeting a cell, tissue, organ or pathogen to be imaged or detected. Exemplary targeting molecules include, but are not limited to, an antibody, antigen-binding antibody fragment, bispecific antibody, affibody, diabody, minibody, ScFvs, aptamer, avimer, targeting peptide, somatostatin, bombesin, octreotide, RGD peptide, folate, folate analog or any other molecule known to bind to a disease-associated target.

Using the techniques described herein, $^{18}$F-labeled molecules of high specific activity may be prepared in a very short time and are suitable for use in imaging techniques. Labeling may occur in a saline medium suitable for direct use in vivo. The labeled molecules are stable under physiological conditions, although for certain purposes, such as kit formulations, a stabilizing agent such as ascorbic acid, trehalose, sorbitol or mannitol may be added.

BACKGROUND

Positron Emission Tomography (PET) has become one of the most prominent functional imaging modalities in diagnostic medicine, with very high sensitivity (fmol), high resolution (4-10 mm) and tissue accretion that can be adequately quantitated. Although [$^{18}$F]2-deoxy-2-fluoro-D-glucose ($^{18}$FDG) is the most widely used PET imaging agent in oncology, there is a keen interest in developing other labeled compounds for functional imaging to complement and augment anatomic imaging methods. Thus, there is a need to have facile methods of conjugating positron emitting radionuclides to various molecules of biological and medical interest.

WO 2011/095150 A1 (corresponding to DE 10210007097 A1) discloses conjugates of $^{18}$F carriers having bioactive organic compounds and their methods of preparation. The carrier comprises a metallocene complex fixed on a solid support, preferably via a phosphine linker. The preparation of the $^{18}$F-labeled targeting molecule requires a multi-step process. First, the metallocene complex is fixed onto the solid support, then $^{18}$F is added to replace the original metal protective groups, typically Cl, with $^{18}$F. Then the Cl$^{-}$ ions and the excess of $^{18}$F are eluted from the solid support. In a next step a targeting molecule is added to the $^{18}$F-labeled metallocene complex fixed on the solid support to bind the targeting molecule to the $^{18}$F-labeled metallocene complex. Finally the labeled targeting molecule is eluted from the solid support, and, after the elution, a purified $^{18}$F-labeled targeting molecule is collected. This latter is suitable for in vivo imaging.

DE 102011109187 A1 discloses conjugation agents useful e.g. for bioassay and in medical diagnosis. The agents comprise a protected Staudinger component that is convertible into unprotected Staudinger component before conjugation reaction, and is linked with carrier by spacer group.

Both the agents of DE 102011109187 A1 and the conjugates of DE 10210007097 A1 (discussed above) disclose bis-cyclopentadienyl titanocene structures bearing on one or both of the cyclopentadienyl rings substituents consisting of only aliphatic chains with terminal functional groups.

Qian, Yanlong, et al., Polyhedron (1993), 12(8), 967-70; Causey, Patrick W. et al, Organometallics (2004), 23, 4486-4494; EP 953580; and EP 955306 disclose bis-cyclopentadienyl titanocene structures bearing on one or both of the cyclopentadienyl rings substituents consisting of aliphatic chains —(CH$_2$)$_n$— with terminal functional groups such as —OH or NH$_3$Cl.

DE 102006054690 A1 discloses substituted metallocene structures including a bis-cyclopentadienyl titanocene having a carboxylate terminal group linked to one of the cyclopentadienyl group via a substituted alkylene chain (compound VIII).

Thus a need exists for a rapid and simple method of $^{18}$F labeling of targeting moieties, such as proteins or peptides, which results in targeting constructs of suitable specific activity and in vivo stability for detection and/or imaging, while avoiding use of solid support, minimizing the requirements for specialized equipment or highly trained personnel and reducing operator exposure to high levels of radiation. Also, a need exists for compounds suitable to be linked to a protein, peptide or other targeting molecule to form precursors of $^{18}$F labeled targeting molecules. A further need exists for pre-packaged kits that could provide compositions required for performing such novel methods.

SUMMARY

In various embodiments, the present invention concerns compounds and methods relating to $^{18}$F- or $^{19}$F-labeled molecules of use for PET or NMR imaging.

One aspect of the present application concerns compounds of general formula (I):

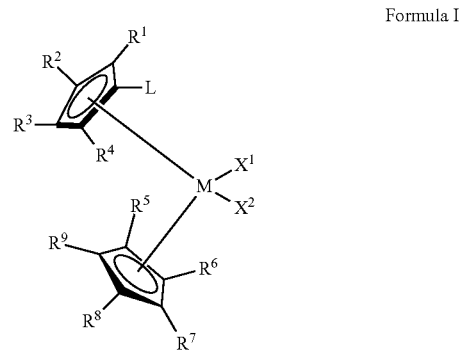

Formula I wherein:

M is a metal selected from the group consisting of titanium, zirconium and hafnium;

$X^1$ and $X^2$, which can be the same or different, are a halogen atom, a R', OR', OCOR', SR', NR'$_2$ or PR'$_2$ group, wherein the R' substituents are linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, $C_7$-$C_{20}$ arylalkyl radicals, optionally containing one or more heteroatoms belonging to the groups 13-17 of the Periodic Table of the Elements;

$X^1$ and $X^2$ can also be interconnected via a cyclic structure of <40 atoms comprising one or more of C, N, O, F, Si, B, P.

$R^1$, $R^2$, $R^3$, $R^4$, $R^5$, $R^6$, $R^7$, $R^8$ and $R^9$, the same or different, are H or linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, $C_7$-$C_{20}$ arylalkyl radicals, optionally containing one or more heteroatoms belonging to the groups 13-17 of the Periodic Table of the Elements.

Two or more adjacent $R^1$, $R^2$, $R^3$, $R^4$, $R^5$, $R^6$, $R^7$, $R^8$ and $R^9$ groups on a cyclopentadienyl residue may be connected by a saturated, or unsaturated bridge containing up to 40 atoms comprising one or more of C, N, S, O, F, Si, B, P. These bridges may contain or be part of up to 5 carbo- or hetero-cycles.

Some examples for such connections are indene or acenaphthene.

$R^1$, $R^2$, $R^3$, $R^4$, $R^5$, $R^6$, $R^7$, $R^8$ and $R^9$ of different cyclopentadienyl residues may be connected by a saturated or unsaturated bridge containing up to 40 atoms comprising C, N, S, O, F, Si, B, P. These bridges may contain or be part of up to 5 carbo- or hetero-cycles.

L is a linker selected from the group consisting of:

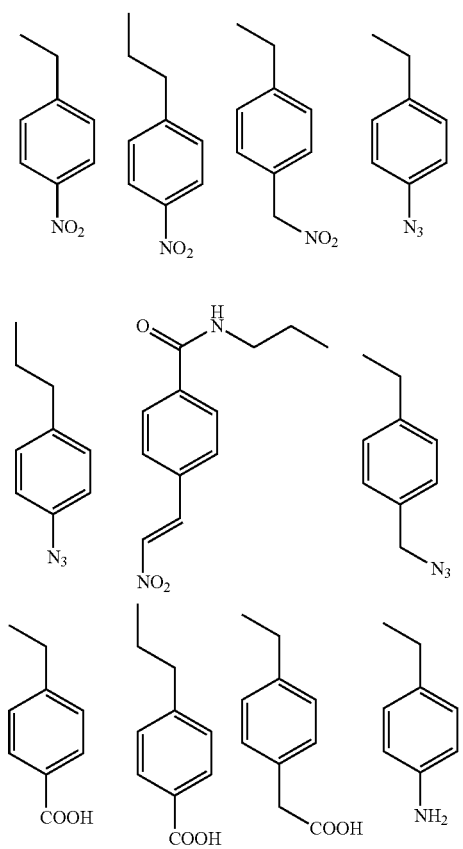

-continued

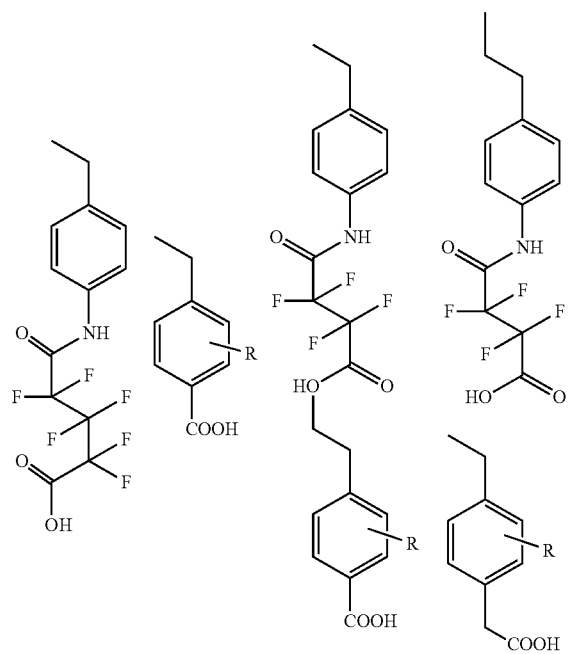

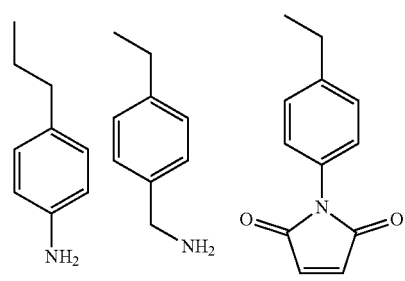

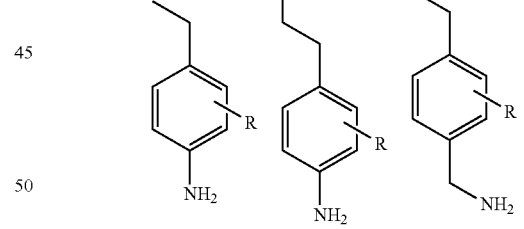

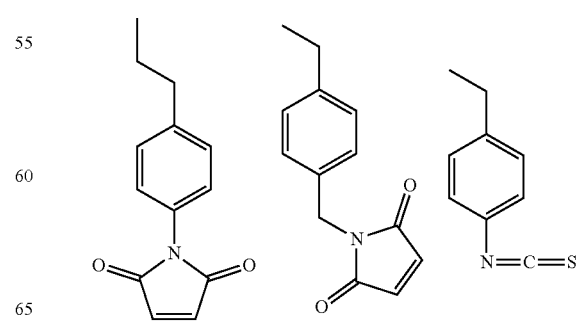

-continued

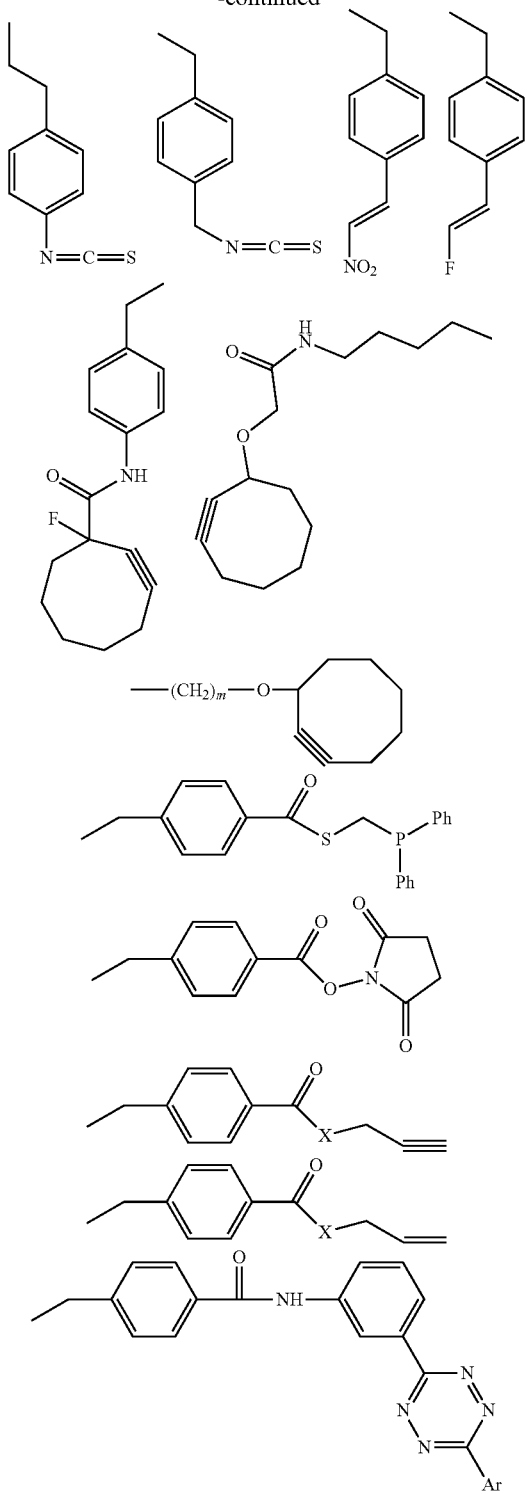

wherein:

Ph=phenyl;

X=R'NH, O, S, in which R' is as defined above;

R is selected from the group consisting of F, CH$_2$F, CHF$_2$, CF$_3$, OCF$_3$;

Ar is C$_6$-C$_{20}$ aryl, C$_7$-C$_{20}$ alkylaryl, or C$_7$-C$_{20}$ arylalkyl radical, optionally containing one or more heteroatoms belonging to the groups 13-17 of the Periodic Table of the Elements.

m=2-20.

Any linker moiety L may be protected at its functional end with a protecting group, as known in the art.

A protective group is advantageous for some linkers to facilitate purification of intermediates or inhibit side reactions on undesired functionalities. A selection of protective group may be found in Theodora Greene et al. Protective groups in synthesis, John Wiley & Sons, Inc, New York, Chichester, Weinheim, Brisbane, Toronto, Singapore, 1999.

As shown in the present examples, the tert-butyl group may act as a protective group for a carboxylic acid group. Many protective groups are known, their choice depends on which group is to be protected and on the protection conditions.

According to another aspect of the present invention, the metallocene complex of Formula (I) above is then attached via the linker group L to a targeting molecule A to form a conjugate of Formula (II):

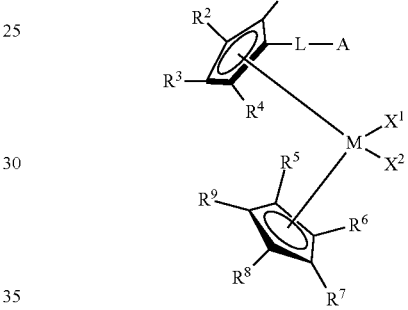

Formula II wherein A is a targeting molecule or recognition element known to bind to a disease-associated target.

The terms "targeting molecule" and "recognition element" are used interchangeably in the present description.

The skilled person will also realize that virtually any targeting or delivery molecule can be attached to $^{18}$F for imaging purposes, so long as it contains derivatizable groups that may be modified without affecting the ligand-receptor binding interaction between the delivery molecule and the cellular or tissue target receptor or the target compound. Although delivery molecules primarily concern peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, siderophores, lipids, etc. may be $^{18}$F-labeled and utilized for imaging purposes.

Certain embodiments involve the use of "click" chemistry for attachment of metallocene complexes of Formula (I) to the targeting molecules A to form conjugates of Formula (II). Preferably, the click chemistry involves the reaction of a targeting molecule such as an antibody or antigen-binding antibody fragment, comprising a functional group such as an alkyne, nitrone or an azide group, with a metallocene comprising the corresponding reactive moiety such as an azide, alkyne or nitrone. Where the targeting molecule comprises an alkyne, the chelating moiety or carrier will comprise an azide, a nitrone or similar reactive moiety. The click chemistry reaction may occur in vitro to form a highly stable, targeting molecule that, after having been labelled with a radionuclide, is then administered to a subject.

According to a further aspect of the present invention, conjugates of Formula (II) are labeled with a radionuclide Y via a fast exchange reaction of $X^1$ and $X^2$. A labeled conjugate of Formula (III) is produced:

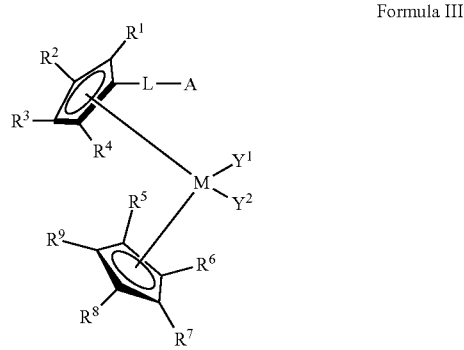

Formula III wherein $Y^1$ and $Y^2$ is a radionuclide, the same or different.

In certain embodiments, molecules that bind directly to receptors, such as somatostatin, octreotide, bombesin, folate or a folate analog, an RGD peptide or other known receptor ligands may be labeled and used for imaging. Receptor targeting agents may include, for example, TA138, a non-peptide antagonist for the integrin αvβ3 receptor (Liu et al., 2003, Bioconj. Chem. 14:1052-56). Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med., Chem. 39:1361-71).

The type of diseases or conditions that may be imaged is limited only by the availability of a suitable delivery molecule for targeting a cell or tissue associated with the disease or condition. Many such delivery molecules are known. For example, any protein or peptide that binds to a diseased tissue or target, such as cancer, may be labeled with $^{18}F$ by the disclosed methods and used for detection and/or imaging. In certain embodiments, such proteins or peptides may include, but are not limited to, antibodies or antibody fragments that bind to tumor-associated antigens (TAAs). Any known TAA-binding antibody or fragment may be labeled with $^{18}F$ by the described methods and used for imaging and/or detection of tumors, for example by PET scanning or other known techniques.

According to a further aspect of the present invention, labeling with the radionuclide is carried out in the liquid phase. The labeled conjugate is then purified and utilized for imaging purposes in the patient. Purification is carried out preferably via HPLC since most of the hospitals with PET imaging equipments have access to HPLC systems suitable to be used with radioactive compounds. Thus, the specialized radio-chemist in the hospital receives the metallocene-targeting molecule conjugate of Formula (II) and, by simply adding the crude $^{18}F$ mixture generated by a cyclotron and performing a HPLC purification, obtains the $^{18}F$-labeled compound of Formula (III) ready to be injected into patients.

A rapid conjugation strategy of a metallocene complex of Formula (I) to obtain conjugates of Formula (II) and Formula (III) can facilitate the diagnosis of a disease. The complex of Formula (I) can be conjugated with a wide variety of recognition elements (A) selective for a certain diseases or subtype thereof. Suitable conjugation chemistry may be chosen among the various forms of "Click chemistry" which have been previously discussed, or the Staudinger reaction (Staudinger, H.; Meyer, J. *Helv. Chim. Acta* 1919, 2, 635-64) performed even on solid phase. (Scabini, M. WO 2011/095150 A1; Kim H. Org. Lett (2006) 8, 1149-1151)

BRIEF DESCRIPTION OF THE DRAWINGS

FIG. 1 is a scheme showing the preparation and use of the compounds according to an embodiment of the invention.

DETAILED DESCRIPTION

The following definitions are provided to facilitate understanding of the disclosure herein. Terms that are not explicitly defined are used according to their plain and ordinary meaning. As used herein, the terms "metallocene complex" or "metallocene compound" are used interchangeably to designate a structure of Formula (I) above.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, the term "pathogen" includes, but is not limited to fungi, viruses, parasites and bacteria, including but not limited to human immunodeficiency virus (HIV), herpes virus, cytomegalovirus, rabies virus, influenza virus, hepatitis B virus, Sendai virus, feline leukemia virus, Reovirus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae, Legionella pneumophila, Streptococcus pyogenes, Escherichia coli, Neisseria gonorrhoeae, Neisseria meningitidis, Pneumococcus, Hemophilus influenzae* B, *Treponema pallidum*, Lyme disease spirochetes, *Pseudomonas aeruginosa, Mycobacterium leprae, Brucella abortus, Mycobacterium tuberculosis* and *Clostridium tetani.*

$^{18}F$ Labeling Techniques

A variety of techniques for labeling molecules with $^{18}F$ are known. Peptide labeling through carbon often involves $^{18}F$-binding to a prosthetic group through nucleophilic substitution, usually in 2- or 3-steps where the prosthetic group is labeled and purified, attached to the compound, and then purified again. This general method has been used to attach prosthetic groups through amide bonds, aldehydes, and "click" chemistry (Marik et al., 2006, Bioconj Chem 17:1017-21; Poethko et al., 2004, J Nucl Med 45:892-902; Li et al., 2007, Bioconj Chem 18:989-93).

A simpler, more efficient $^{18}F$-peptide labeling method was developed by Poethko et al. (2004), where a 4-$^{18}F$-fluorobenzaldehyde reagent was conjugated to a peptide through an oxime linkage in about 75-90 min, including the dry-down step. The newer "click chemistry" method attaches $^{18}F$-labeled molecules onto peptides with an acetylene or azide in the presence of a copper catalyst (Li et al, 2007; Glaser and Arstad, 2007, Bioconj Chem 18:989-93). The reaction between the azide and acetylene groups forms a triazole connection, which is quite stable and forms very efficiently on peptides without the need for protecting groups. Click chemistry produces the $^{18}$F-labeled peptides in good yield (50%) in about 75-90 min with the dry-down step.

In the present description and examples new metallocene compounds that conjugate with targeting molecules are disclosed to provide an improved method for $^{18}$F-labeling of peptides and other molecules of use in PET imaging.

Metallocene Complex of Formula (I)

According to an aspect of the present invention a metallocene complex of Formula (I) is used to prepare an $^{18}$F-labeled molecule for in vivo imaging:

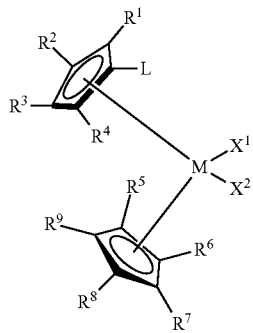

Formula (I)

wherein M, $X^1$, $X^2$, L, $R^1$, $R^2$, $R^3$, $R^4$, $R^5$, $R^6$, $R^7$, $R^8$ and $R^9$ are as defined above.

The metal M is preferably titanium or zirconium, more preferably titanium.

$R^1$, $R^2$, $R^3$, $R^4$, $R^5$, $R^6$, $R^7$, $R^8$ and $R^9$, which can be the same or different, are preferably selected from the group consisting of H, metyl, benzyl, isobutyl, tert-butyl, methoxy, trimetylsilyl, 1,3-butadiene-1,4-diyl, as represented below:

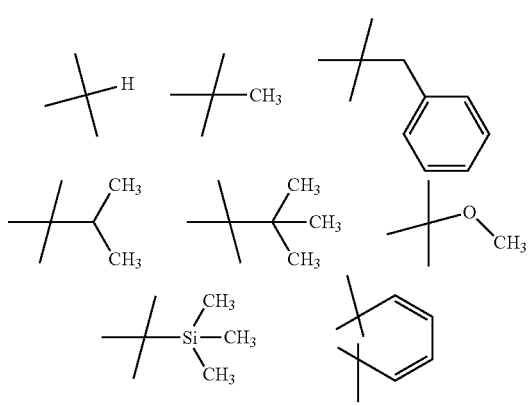

$R^1$, $R^2$, $R^3$, $R^4$, $R^5$, $R^6$, $R^7$, $R^8$ and $R^9$ are more preferably H, methyl, or benzyl.

$X^1$ and $X^2$ are preferably selected from F, Cl, Br, I, alkynes, OR" or SR", wherein R" is a divalent radical selected from the group consisting of $C_6$-$C_{20}$ arylidene being either unsubstituted or substituted with a group comprising 2-40 C, N, O, F, Si, B, P atoms. Preferred alkynes are:

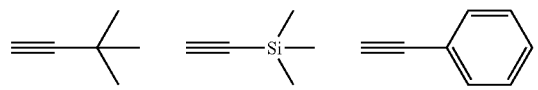

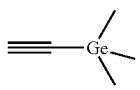

Other examples of groups $X^1$ and $X^2$ are carboxylate, thiocarboxylate, dithiocarboxylate, carbamate, thiocarbamate, dithiocarbamate, trithiocarbamate, thiophosphinate dithiophosphinate, thiophosphonate, dithiophosphonate, trithiophosphonate, thiophosphate, dithiophosphate, trithiophosphate, tetrathiophosphate, sulfonate, thiosulfonate.

Still other examples of groups $X^1$ and $X^2$ are heterocycles such as imidazole, triazole, tetrazol, thiazol, benzimidazol, benzotriazol, indole, indazole, pyrazole, pyrrolidon, azetan, azepine, benzodiazepine, pipeidine, purin, morpholine, piperazine, triazine, oxazole, hydantoine, aziridine, pyrrolidine, pyrrole, hexamethyeneimine, azaindoles or alkylated, acylated, arylated, annulated or heteroannulated members of this group having pKa<12.

As defined above, $X^1$ and $X^2$ can also be interconnected via a cyclic structure of <40 atoms comprising one or more of C, N, O, F, Si, B, P.

$X^1$ and $X^2$, which can be the same or different, are more preferably benzene-1,2-dithiolate, ethanethiolate, benzoate, 3,3-dimethyl-1-butyne, chlorine, fluorine, pentasulfide.

L is a linker selected from the group consisting of:

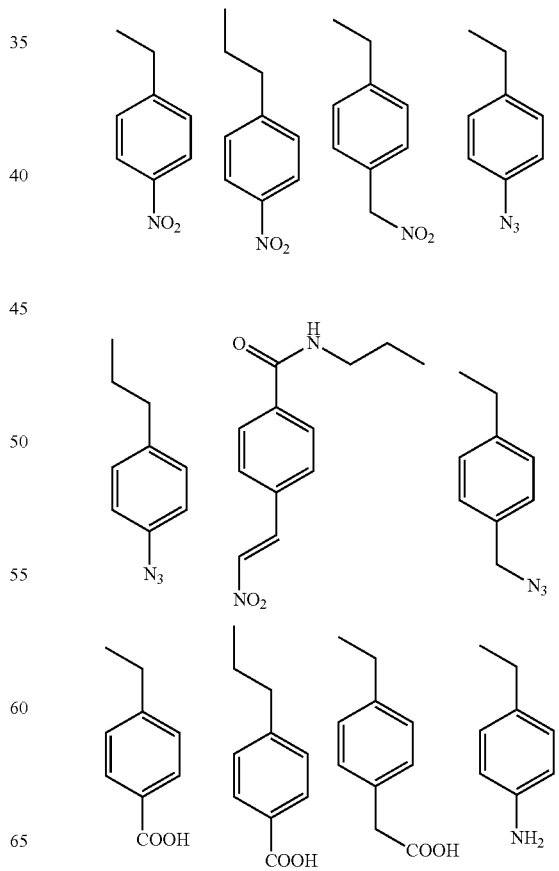

11
-continued
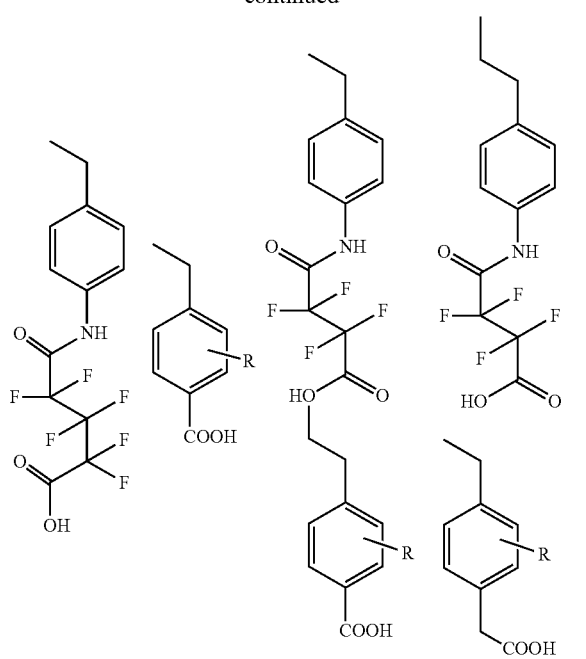
12
-continued
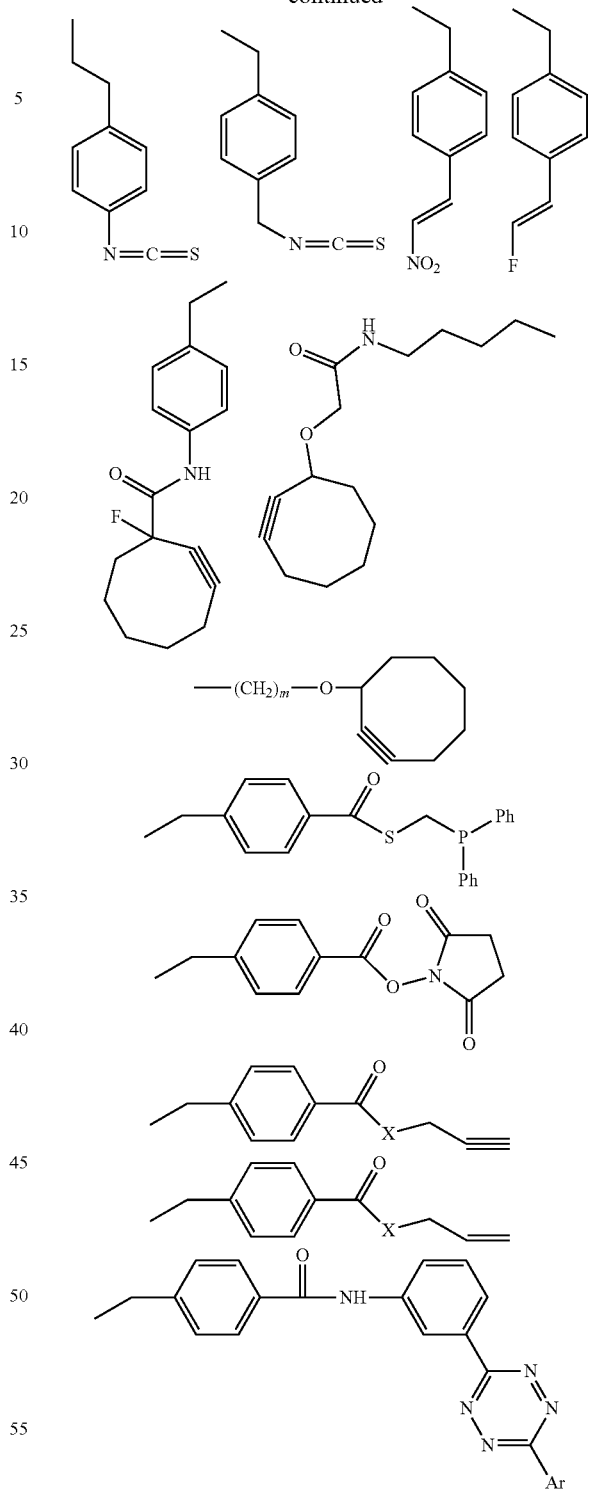
wherein:
Ph=phenyl;
X=R'NH, O, S, in which R' is as defined above;
R is selected from the group consisting of F, $CH_2F$, $CHF_2$, $CF_3$, $OCF_3$;
Ar is $C_6$-$C_{20}$ aryl, $C_7$-$C_{20}$ alkylaryl, or $C_7$-$C_{20}$ arylalkyl radical, optionally containing one or more heteroatoms belonging to the groups 13-17 of the Periodic Table of the Elements.

m=2-20.

Preferably 4≤m≤12, more preferably m=6.

As it appears from the list above, the linker group L according to the invention comprises an arylene moiety incorporated in the linker structure, typically a phenylene moiety, and/or a cyclooctyne terminal group.

Conjugate of Formula (II)

According to an aspect of the present invention a metallocene complex of Formula (I) is used to prepare a conjugate with a targeting molecule or recognition element A via the linker group L.

The substituent L, or linker group L, bears a terminal functional group that can react with a corresponding functional group of a targeting molecule A, so that a compound or conjugate of Formula (II) can be formed:

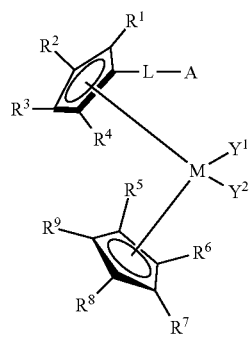

Formula (II)

The meaning of the substituents is as given above.

Preferred terminal groups for the linker L are phosphine, azide, alkene, alkyne, carboxylic acid, carboxylic ester, phosphoramidite, H-phosphonatealdehyde, ketone, chloroimidate, thiol, or a chelator that is able to complex an ion together with the molecule A.

A particularly preferred linker group L is —CH$_2$—Ar—COO— bearing a terminal group as defined above.

Another particularly preferred linker group L is

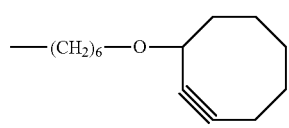

Preferred compounds of Formula (I) are listed below:

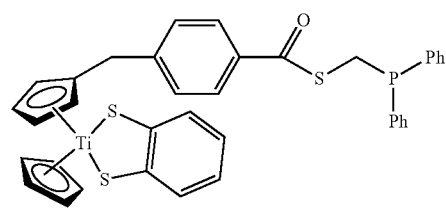

(Ia)

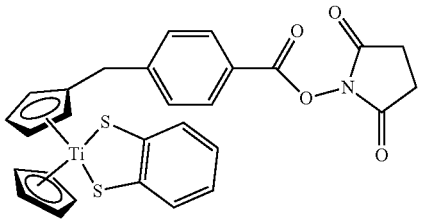

(Ib)

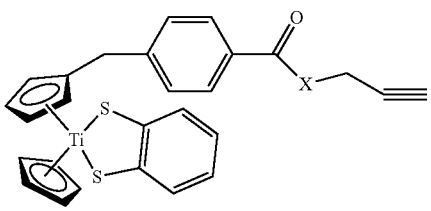

(Ic)

X = RNH, O

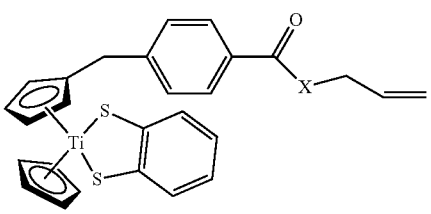

(Id)

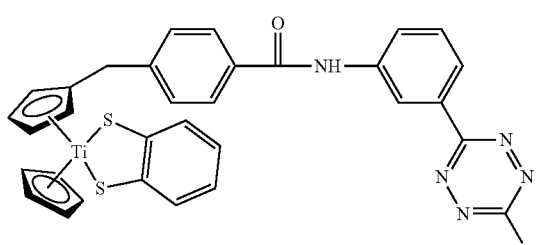

(Ie)

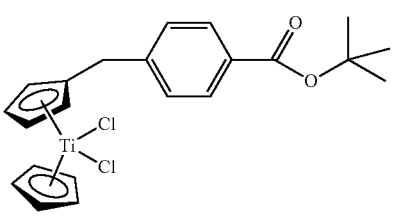

(If)

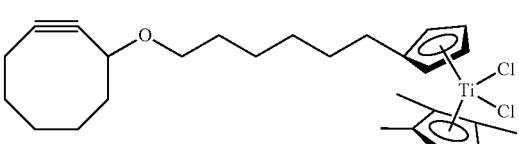

(Ig)

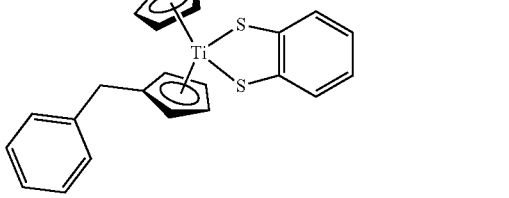

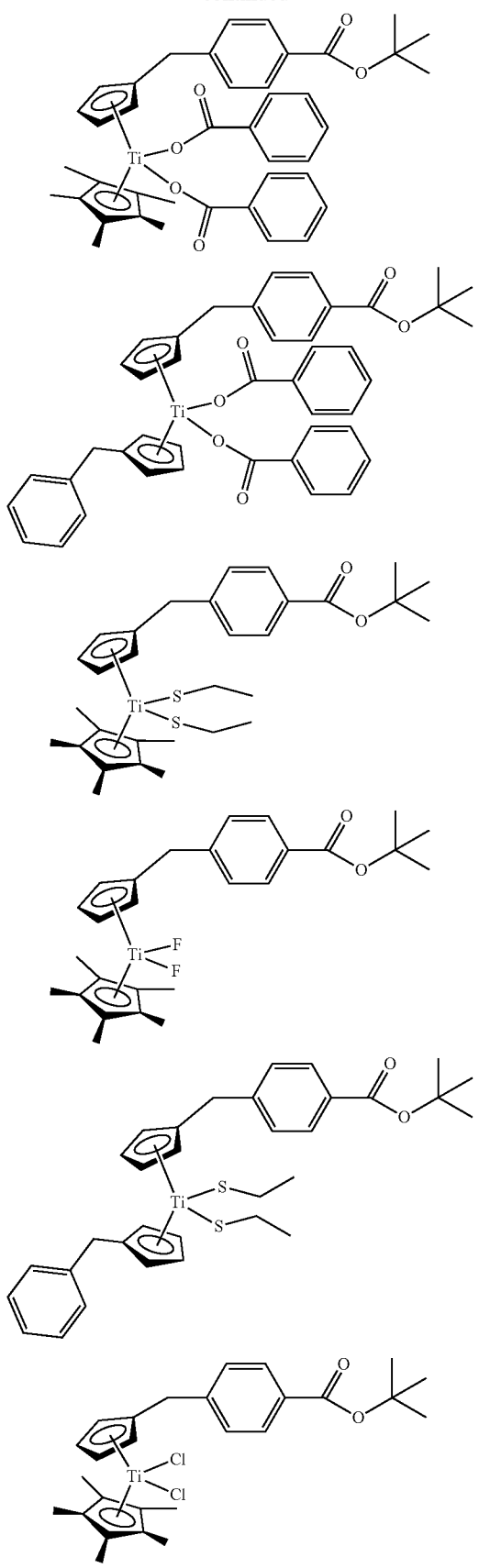
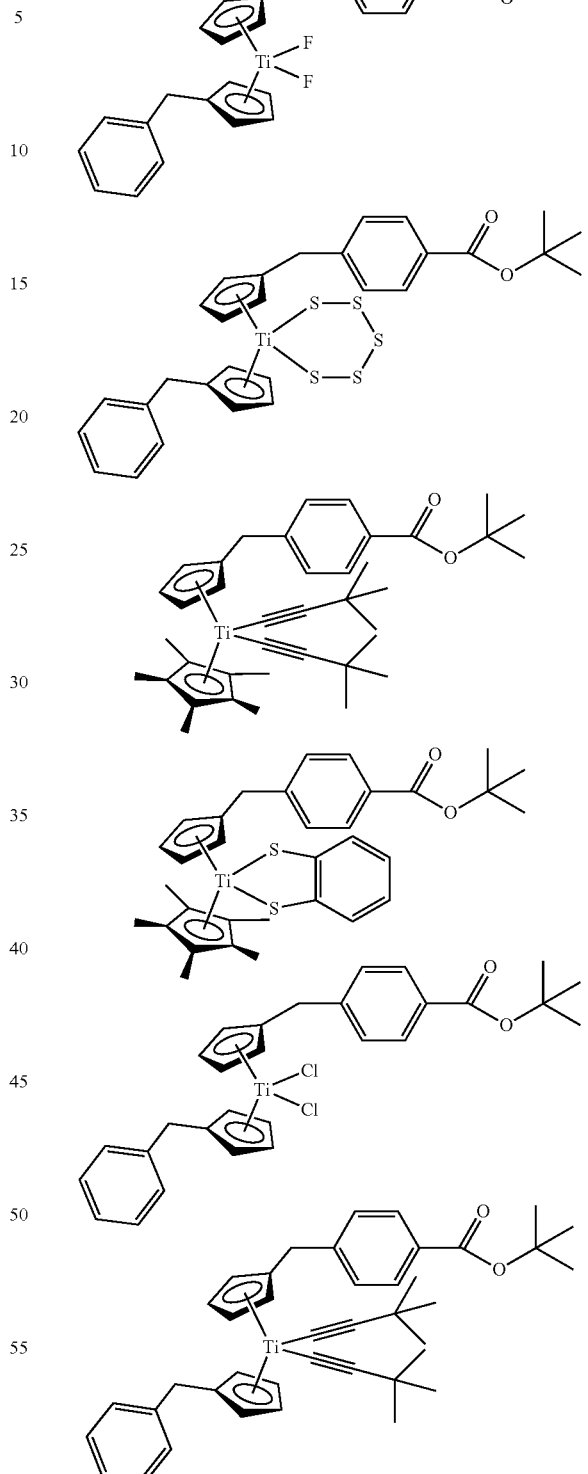
wherein:
Ph=phenyl;
X=R'NH, in which R' is as defined above;
R is selected from the group consisting of F, CH₂F, CHF₂, CF₃, OCF₃;

Ar is $C_6$-$C_{20}$ aryl, $C_7$-$C_{20}$ alkylaryl, or $C_7$-$C_{20}$ arylalkyl radical, optionally containing one or more heteroatoms belonging to the groups 13-17 of the Periodic Table of the Elements.

Methods of preparation of compound of Formula (I)

Compounds of Formula (I) can be generally synthesized as described below.

The synthesis begins with a cyclopentadiene bearing from 0 to 5 alkyl substituents, $R^5$-$R^9$. This compound exists as a readily interconvertible mixture of tautomers. The mixture of tautomers is then deprotonated using a strong base such as BuLi, sec-BuLi or tert-Bu Li, but not necessarily a Li-base. The resulting Lithium cyclopentadienide is then transmetallated with $TiCl_4$ to give a cyclopentadienyl trichloro titanium complex.

This latter is reacted with an equivalent of another deprotonated cyclopentadiene such as one bearing $R^1$-$R^4$ and L (which also exits as a mixture of tautomers in its protonated form), wherein L is the linker group defined in Formula 1.

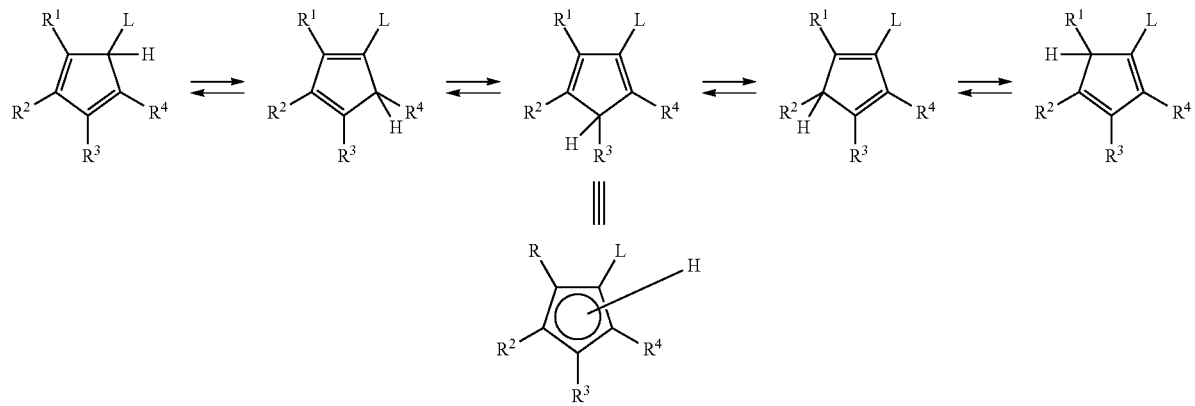

L is suitably protected to avoid unwanted reactions with the cyclopentadienyl titanium trichloride or the Li-cyclopentadienide.

The product of this reaction is a titanocenyl dichloride bearing two cyclopentadienyl residues, one with the groups $R^1$-$R^5$ and the other with the groups $R^6$-$R^9$ and L. If the titanocene dichloride has sufficient stability in serum and allows rapid displacement with $^{18}F$, its L-protective group is then removed to allow conjugation with the recognition element A. If the titanocene dichloride has insufficient stability in serum or cannot be easily substituted by $^{18}F$, the chloro groups will have to be displaced by other, more suitable leaving groups like benzendithiole-groups representing $X^1$ and $X^2$. In some cases the displacement of Cl by $X^1$ and $X^2$ may be sequential. The same is true for the substitution of $X^1$ and $X^2$ with radioisotopes $Y^1$ and $Y^2$. It is most likely that during the radioactive decay one of the groups $Y^1$ and $Y^2$, which were initially the same, will be converted into another element before the other.

The protective group of the linker L is then removed to allow conjugation with the recognition element.

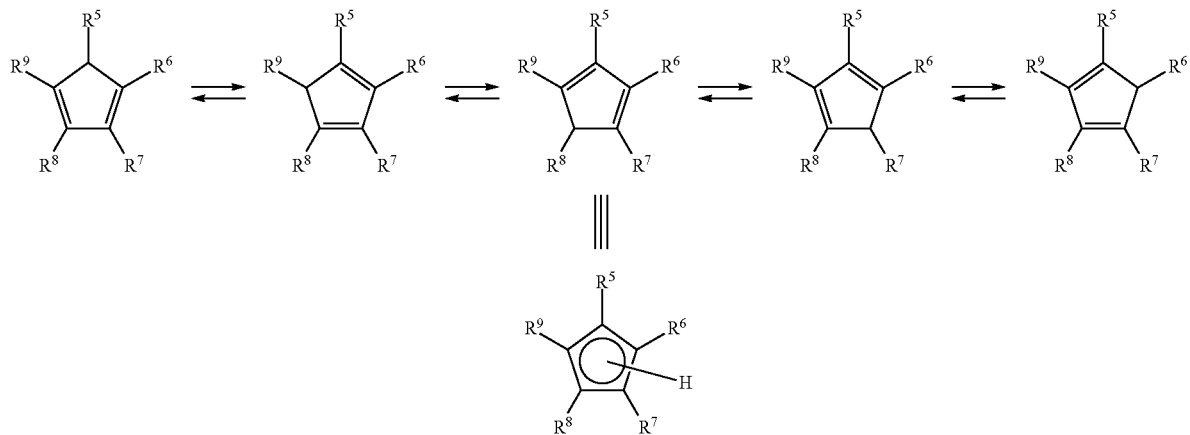

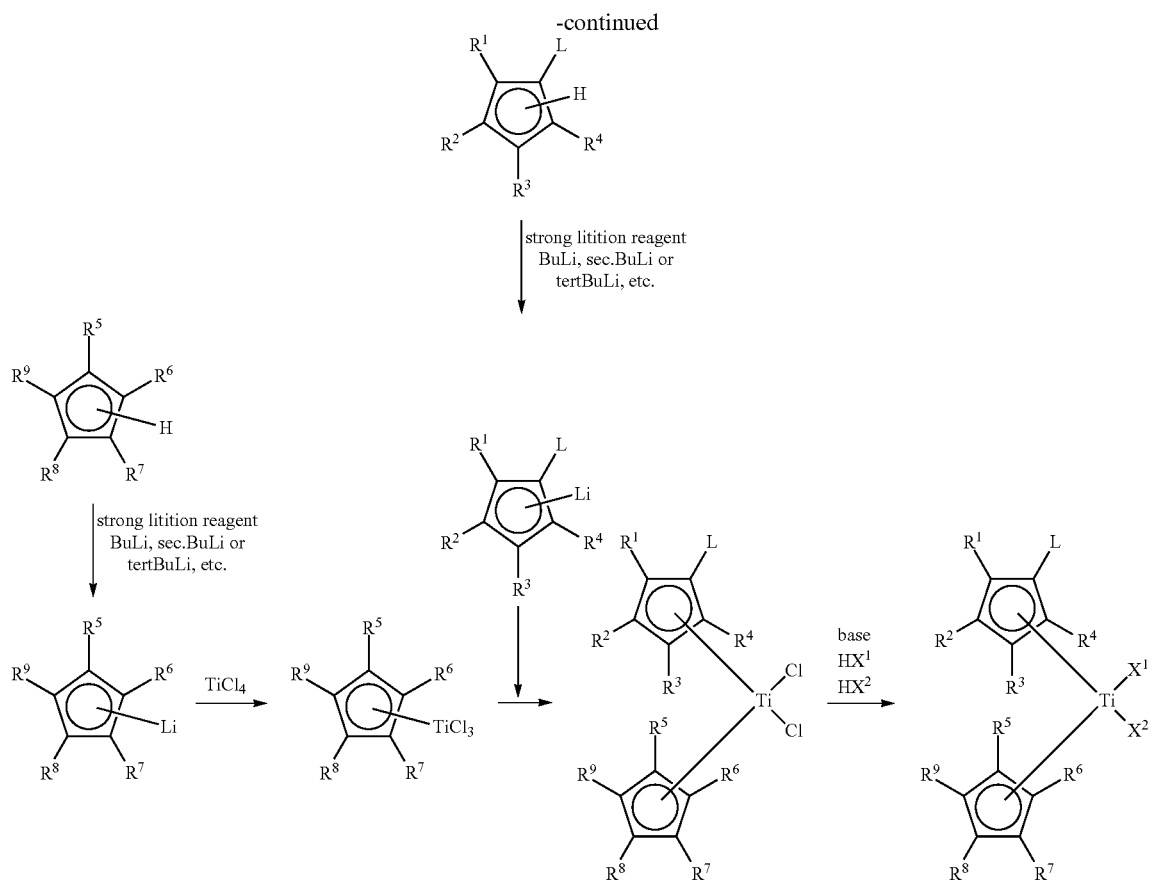

Methods of Preparation of Compound of Formula (II)

Click Chemistry

In various embodiments, conjugates of Formula (II) may be prepared from metallocene compounds of Formula (I) and targeting molecules A using the click chemistry technology. The click chemistry approach was originally conceived as a method to rapidly generate complex substances by joining small subunits together in a modular fashion. (See, e.g., Kolb et al., 2004, Angew Chem Int Ed 40:3004-3); Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

Staudinger Reaction

Chemoselective ligation such as the Staudinger ligation (azide-phosphine) can also be used to prepare conjugates of Formula (II) from metallocene compounds of Formula (I) and targeting molecules A. Of these reaction types, the Staudinger chemistry has the best efficiency and compatibility for live-cell labeling and mass spectrometry (MS) applications for biological research.

The Staudinger reaction occurs between a methyl ester phosphine (P3) and an azide (N3) to produce an aza-ylide intermediate that is trapped to form a stable covalent bond. This crosslinking chemistry has been applied to biological systems as a bioconjugation technique (Saxon and Bertozzi, 2000). The chemical biology application is now known as Staudinger ligation. Unlike typical crosslinking methods used in biological research, this reaction chemistry depends upon a pair of unique reactive groups that are specific to one another and also foreign to biological systems. Because phosphines and azides do not occur in cells, they react only with each other in biological samples, resulting in minimal background and few artifacts. This is the meaning of "chemoselective".

Modifications of click chemistry reactions are suitable for use in vitro or in vivo. Reactive targeting molecule may be formed by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above. Alternatively, methods of chemical conjugation of such moieties to biomolecules are well known in the art, and any such known method may be utilized. The disclosed techniques may be used in combination with the $^{18}$F or $^{19}$F labeling methods described below for PET or NMR imaging, or alternatively may be utilized for delivery of any therapeutic and/or diagnostic agent that may be conjugated to a suitable activated targetable construct and/or targeting molecule.

Targetable Constructs

In certain embodiments, the moiety labeled with $^{18}$F or other diagnostic and/or therapeutic agents may comprise a peptide or other targetable construct. Labeled peptides (or proteins), for example RGD peptide, octreotide, bombesin or somatostatin, may be selected to bind directly to a targeted cell, tissue, pathogenic organism or other target for imaging, detection and/or diagnosis. In other embodiments, labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue. The distribution of $^{18}$F-labeled targetable constructs may be determined by PET scanning or other known techniques.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and coupled to metallocene complexes substituted with suitable linker groups. The linker should be a low molecular weight moiety, preferably having a molecular weight of less than 50,000 daltons, and advantageously less than about 20,000 daltons, 10,000 daltons or 5,000 daltons. More usually, the targetable construct peptide will have four or more residues.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.).

Antibodies
Target Antigens

Targeting antibodies of use may be specific to or selective for a variety of cell surface or disease-associated antigens. Exemplary target antigens of use for imaging or treating various diseases or conditions, such as a malignant disease, a cardiovascular disease, an infectious disease, an inflammatory disease, an autoimmune disease, a metabolic disease, or a neurological (e.g., neurodegenerative) disease may include α-fetoprotein (AFP), A3, amyloid beta, CA125, colon-specific antigen-p (CSAp), carbonic anhydrase IX, CCCL19, CCCL21, CSAp, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, CEACAM5, CEACAM6, c-met, B7, ED-B of fibronectin, EGP-1, EGP-2, Factor H, FHL-1, fibrin, Flt-3, folate receptor, glycoprotein GRO-β, human chorionic gonadotropin (HCG), HER-2/neu, HMGB-1, hypoxia inducible factor (HIP), HM1.24, HLA-DR, Ia, ICAM-1, insulin-like growth factor-1 (IGF-1), IGF-1R, IFN-γ, IFN-α, IFN-β, IL-2, IL-4R, IL-6R, IL-13R, IL-15R, IL-17R, IL-18R, IL-1, IL-6, IL-8, IL-12, IL-15, IL-17, IL-18, IL-25, IP-10, KS-1, Le(y), low-density lipoprotein (LDL), MAGE, mCRP, MCP-1, MIP-1A, MIP-1B, MIF, MUC1, MUC2, MUC3, MUC4, MUC5a-c, MUC16, NCA-95, NCA-90, as NF-κB, pancreatic cancer mucin, PAM4 antigen, placental growth factor, p53, PLAGL2, Pr1, prostatic acid phosphatase, PSA, PRAME, PSMA, PIGF, tenascin, RANTES, T101, TAC, TAG72, TF, Tn antigen, Thomson-Friedenreich antigens, thrombin, tumor necrosis antigens, TNF-α, TRAIL receptor (R1 and R2), TROP2, VEGFR, EGFR, complement factors C3, C3a, C3b, C5a, C5, and an oncogene product.

Methods for Raising Antibodies

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 6: 3833 (1989). Techniques for constructing chimeric antibodies are well known to those of skill in the art. As an example, Leung et al., Hybridoma 13:469 (1994), produced an LL2 chimera by combining DNA sequences encoding the Vκ and VH domains of murine LL2, an anti-CD22 monoclonal antibody, with respective human κ and IgG1 constant region domains.

Humanized Antibodies

Techniques for producing humanized MAbs are well known in the art (see, e.g., Jones et al., Nature 32): 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844

(1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50). A fully human antibody also can be constructed by genetic or chromosomal transfection methods, as well as phage display technology, all of which are known in the art. See for example, McCafferty et al., Nature 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, Genet. Mol. Res. 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, J. Immunol. Methods 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

Known Antibodies

The skilled person will realize that the targeting molecules of use for imaging, detection and/or diagnosis may incorporate any antibody or fragment known in the art that has binding specificity for a target antigen associated with a disease state or condition. Such known antibodies include, but are not limited to, hR1 (anti-IGF-1R, U.S. patent application Ser. No. 12/772,645, filed Mar. 12, 2010) hPAM4 (anti-pancreatic cancer mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,662,378, U.S. patent application Ser. No. 12/846,062, filed Jul. 29, 2010), hRS7 (anti-TROP2, U.S. Pat. No. 7,238,785), hMN-3 (anti-CEACAM6, U.S. Pat. No. 7,541,440), Ab124 and Ab125 (anti-CXCR4, U.S. Pat. No. 7,138,496.

Antibodies of use may be commercially obtained from a wide variety of known sources. For example, a variety of antibody secreting hybridoma lines are available from the American Type Culture Collection (ATCC, Manassas, Va.). The skilled person will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Fragments

Antibody fragments which recognize specific epitopes can be generated by known techniques. The antibody fragments are antigen binding portions of an antibody, such as F(ab')2, Fab', F(ab)2, Fab, Fv, sFv and the like. F(ab')2 fragments can be produced by pepsin digestion of the antibody molecule and Fab' fragments can be generated by reducing disulfide bridges of the F(ab')2 fragments. Alternatively, Fab' expression libraries can be constructed (Huse et al., 1989, Science, 246:1274-1281) to allow rapid and easy identification of monoclonal Fab' fragments with the desired specificity. An antibody fragment can be prepared by proteolytic hydrolysis of the full length antibody or by expression in *E. coli* or another host of the DNA coding for the fragment. These methods are described, for example, by Goldenberg, U.S. Pat. Nos. 4,036,945 and 4,331,647 and references contained therein, which patents are incorporated herein in their entireties by reference. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Immunoconjugates

Any of the antibodies, antibody fragments or antibody fusion proteins described herein may be conjugated to a metallocene complex of Formula (I) to form an immunoconjugate of Formula (II). Methods for covalent conjugation of substituted metallocene complexes having linker moieties L are described above.

Affibodies

Affibodies are small proteins that function as antibody mimetics and are of use in binding target molecules. Affibodies were developed by combinatorial engineering on an alpha helical protein scaffold (Nord et al., 1995, Protein Eng 8:601-8; Nord et al., 1997, Nat Biotechnol 15:772-77). The affibody design is based on a three helix bundle structure comprising the IgG binding domain of protein A (Nord et al., 1995; 1997). Affibodies with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins.

The skilled person will realize that affibodies may be used as targeting molecules in the practice of the claimed methods and compositions. Labeling with metal-conjugated 18F having linker moieties L may be performed as described above. Affibodies are commercially available from Affibody AB (Solna, Sweden).

Phage Display Peptides

In some alternative embodiments, binding peptides may be produced by phage display methods that are well known in the art. For example, peptides that bind to any of a variety of disease-associated antigens may be identified by phage display panning against an appropriate target antigen, cell, tissue or pathogen and selecting for phage with high binding affinity.

Various methods of phage display and techniques for producing diverse populations of peptides are well known in the art. For example, U.S. Pat. Nos. 5,223,409; 5,622,699 and 6,068,829, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that may serve as leads to the development of peptidomimetic drugs or imaging agents (Arap et al., 1998a, Science 279:377-380). In addition to peptides, larger protein domains such as single-chain antibodies may also be displayed on the surface of phage particles (Arap et al., 1998a).

Apomers

In certain embodiments, a targeting molecule may comprise an aptamer. Methods of constructing and determining the binding characteristics of aptamers are well known in the art. For example, such techniques are described in U.S. Pat. Nos. 5,582,981, 5,595,877 and 5,637,459.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred. Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate. Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports.

Methods for preparation and screening of aptamers that bind to particular targets of interest are well known, for example U.S. Pat. No. 5,475,096 and U.S. Pat. No. 5,270,163. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target.

Avimers

In certain embodiments, the targeting molecules may comprise one or more avimer sequences. Avimers are a class of binding proteins somewhat similar to antibodies in their affinities and specificities for various target molecules. They were developed from human extracellular receptor domains by in vitro exon shuffling and phage display (Silverman et al., 2005, Nat. Biotechnol. 23:)493-94; Silverman et al., 2006, Nat. Biotechnol. 24:220). The resulting multidomain proteins may comprise multiple independent binding domains, that may exhibit improved affinity (in some cases sub-nanomolar) and specificity compared with single-epitope binding proteins. (Id.) Additional details concerning methods of construction and use of avimers are disclosed, for example, in U.S. Patent Application Publication Nos. 20040175756, 20050048512, 20050053973, 20050089932 and 20050221384.

Solid State Preparation

Depending on the nature of the recognition element A, the conjugate of Formula (II) can also be prepared by reacting the recognition element A in the solid state with the complex of Formula (I).

An example is a peptide like octreotide, which is synthesized on solid phase and may be attached to the complex of Formula (I), while still being bound to the synthesis resin. Subsequently, it may be released from the solid phase as conjugate of Formula (II). Other applications may include proteins or oligonucleotides either synthesized on a synthesis support or isolated bound to some reactive affinity matrix.

Method of Labeling with $^{18}F$

Conjugates of Formula (II) can be labeled with $^{18}F$ via a fast $^{18}F$ exchange to prepare a labeled conjugate of Formula (III):

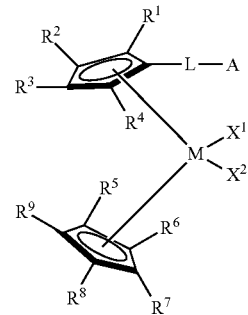

Formula III wherein the meaning of the substituents $R^1$, $R^2$, $R^3$, $R^4$, $R^5$, $R^6$, $R^7$, $R^8$, $R^9$, M and L is as given above.

$Y^1$ and $Y^2$ is a radionuclide which, can be introduced to displace $X^1$ and $X^2$ by direct bond with M, as it is preferably done with $^{18}$F (110m), $^{120}$I (81.0 m), $^{124}$I (4.18 d), or $^{76}$Br (16.2 h). The displacement is performed immediately prior to usage to minimize loss of labeling due to radioactive decay.

Y is preferably $^{18}$F.

According to an aspect of the present invention, labeling with the radionuclide is carried out in the liquid phase.

In the present description the terms "radionuclide" and "tracer" are used interchangeably.

The introduction of the $^{18}$F tracer with a half life of 110 min. has to proceed rapidly, i.e. in less than three half-lives. The labeling temperature is below 100° C. The preferred labeling temperature is low enough to avoid irreversible damage of the tracer conjugate.

The environment (solvent) of the label is equally important. $^{18}$F is most commonly available in aqueous solutions as K$^{18}$F. In organic solutions, such as in acetonitrile, the positive counterion (K$^+$-ion) is generally complexed with suitable complexing agents, such as the cryptands commercially available under the tradename "Kryptofix" (Merck KGAA) to obtain dissolution.

The high radioactivity involved in the introduction of the tracer requires special safety measures to protect the laboratory personnel. The labeling process has to meet these requirements by comprising as few manipulations as possible. In particular many solvent exchanges, reactions at or above boiling point of the solvent or reactions under pressure should be avoided or minimized since they pose a great risk of contamination. Therefore one pot procedures, possibly using immobilized reagents, are preferred (Langstrom, B. et al., *Acta Chem. Scand.* 1999, 53, 651; Miller, P. M. et al. *Angew. Chem. Int. Ed.* 2008, 47, 8998).

The waste, often containing excess radiolabel, must be in the most concentrated form to allow safe disposal, separate from non-radioactive wastes. (C. S. Elmore, *Ann. Rep. Med. Chem.* 2009, 44, 515).

Consequently, the following processes are performed at low temperature at a high reaction rate using the $^{18}$F-sources that are generally obtained from a cyclotron. As said above, the processes may even be performed on a conjugate of Formula (II) immobilized on a solid phase. An immobilization via hydrophobic contacts on a hydrophobic stationary phase, resistant to fluoride, is preferred. Preferred stationary phases are C-18 analogous phases based on polystyrene, polyacrylamide or polypropylene and can be obtained from commercial sources even in SPE-cartridge form.

One embodiment of the general process is as follows:
a) A specialized radio-chemist in the hospital receives the metallocene-targeting molecule conjugate of Formula (II) and loads it onto cartridge containing a stationary phase as described above.
b) Then an acidified OF-solution obtained from a cyclotron is added. The excess of fluoride is eluted rapidly from the column. The $X^1$-$X^2$ groups, for example benzene dithiol, remain at the starting point of the cartridge.
c) Then the $^{18}$F-labelled conjugate of Formula (III) is eluted from the column using fluoride-free buffer and acetonitrile at physiological pH.
d) The displaced $X^1$-$X^2$ groups, for instance the benzene dithiol, are washed off the cartridge using a high concentration of an non-polar solvent, such as acetonitrile.

The progress of the thiol-fluoride exchange may be visually monitored by the color change (in case of a displacement of benzene dithiol groups by fluoride, the titanocene absorbance maximum of 450 and 600 nm disappears. This is valid for all compounds with a cyclopentadienyl titanium chromophore.

The facile labeling-method allows to provide a product that meets the specifications necessary for tracer injection.

In case of solution-phase labeling, or unsatisfactory purity criteria after a solid-phase labeling, a further HPLC purification to obtain the $^{18}$F-labeled compound of Formula (III) may be performed prior to injection into patients.

These labeled, purified conjugates can then be used for imaging purposes in the patient. Purification is carried out preferably via HPLC since most of the hospitals with PET imaging equipments have access to HPLC systems suitable to be used with radioactive compounds.

Formulation and Administration

The $^{18}$F-labeled molecules may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the $^{18}$F-labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection. Injection may be intravenous, intraarterial, intralymphatic, intrathecal, subcutaneous or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising $^{18}$F-labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate or citrate and the like. In certain preferred embodiments, the buffer is potassium biphthalate (KHP), which may act as a transfer ligand to facilitate $^{18}$F-labeling. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

In general, the dosage of $^{18}$F label to administer will vary depending upon such factors as the patient's age, weight, height, sex, general medical condition and previous medical history. Preferably, a saturating dose of the 18F-labeled molecules is administered to a patient. For administration of 18F-labeled molecules, the dosage may be measured by millicuries. A typical range for 18F imaging studies would be five to 10 mCi.

Administration of Peptides

Various embodiments of the claimed methods and/or compositions may concern one or more $^{18}$F-labeled peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection. Where, for example, $^{18}$F-labeled peptides are administered in a pretargeting protocol, the peptides would preferably be administered i.v.

Imaging Using Labeled Molecules

Methods of imaging using labeled molecules are well known in the art, and any such known methods may be used with the $^{18}$F-labeled molecules disclosed herein. See, e.g., U.S. Pat. Nos. 6,241,964; 6,358,489; 6,953,567 and published U.S. Patent Application Publ. Nos. 20050003403; 20040018557; 20060140936. See also, Page et al., Nuclear Medicine And Biology, 21:911-919, 1994; Choi et al., Cancer Research 55:5323-5329, 1995; Zalutsky et al., J. Nuclear Med., 33:575-582, 1992; Woessner et. al. Magn. Reson. Med. 2005, 53: 790-99.

Kits

Various embodiments of the invention concern kits containing components suitable for imaging, diagnosing and/or detecting diseased tissue in a patient using labeled compounds. Exemplary kits may contain an antibody, fragment or fusion protein, such as a bispecific antibody of use in pretargeting methods as described herein. Other components may include a targetable construct for use with such bispecific antibodies.

In preferred embodiments, the targetable construct is preconjugated to a metallocene complex that may be used to attach an $^{18}$F radionuclide. However, in alternative embodiments it is contemplated that a targetable construct may be attached to one or more different radionuclide, as described above.

A device capable of delivering the kit components may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

Preparation of Compound of Formula (If)

Step 1: Preparation of t-butyl 4-(bromomethyl)benzoate

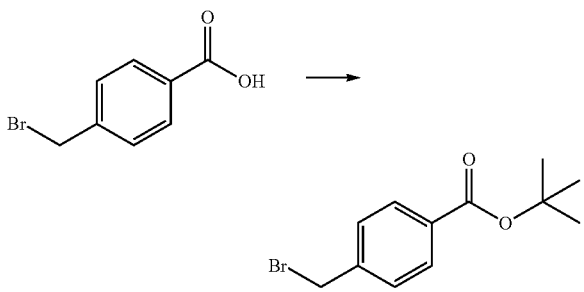

4.15 mmoles (1 g) of 4-(bromomethyl) benzoic acid were dissolved in a mixture of cyclohexane (9 ml), dichloromethane (4.75 ml) and tetrahydrofuran (THF, 0.5 ml). The mixture was kept under a static atmosphere of argon. A solution of tert-butyl-2,2,2-trichloroacetamidate (1.68 ml, 9.02 mmoles, 2 equivalents) in cyclohexane (3 mL) was added dropwise.

A catalytic amount of $BF_3.Et_2O$ was then added.

The reaction mixture was stirred for 18 hours at room temperature. Progress of the reaction was monitored via thin layer chromatography (TLC) (hexane-AcOEt 8:2). Upon completion the reaction was terminated by adding $NaHCO_3$ (1 g).

The reaction mixture was then filtered and concentrated at reduced pressure.

The raw reaction product was purified on a silica gel column (25 g) using hexane-diethyl ether (9:1) as diluent.

1H-NMR (200 MHz): δ 7.98 (d, 2H), 7.45 (d, 2H), 4.50 (s, 2H), 1.54 (s, 9H).

Step 2: Preparation of t-butyl 4-(cyclopentadiene-1-ylmethyl)benzoate

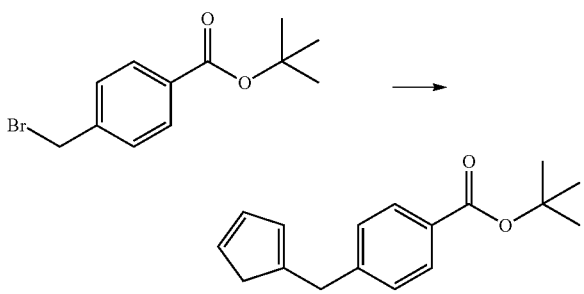

0.96 ml (1.91 mmoles, 1 eqv) of sodium cyclopentadienide were introduced in a anhydrous 2-neck flask under a static atmosphere of argon and brought to −78° C. A solution of t-butyl 4-(bromomethyl)benzoate (2.11 mmoles, 571 mg, 1.1 eqv) in THF (2.5 ml) was slowly added dropwise. When the solution gradually reached the room temperature it was kept under stirring for about 1 hour.

A saturated solution of $NH_4Cl$ (3 ml) and hexane (5 ml) was added and the phases were separated. The aqueous phase was extracted with hexane (3×5 ml) and the organic phases were mixed. Drying on $Na_2SO_4$ was then carried out, followed by filtration and concentration at reduced pressure.

The obtained raw product was purified on a column of silica gel (30 g) using a mixture of hexane diethyl ether (9:1) as eluent.

$^1$H-NMR (200 MHz): δ 7.98 (d, 2H), 7.25 (d, 2H), 6.48-6.05 (m, 3H), 3.76 (d, 2H), 2.98-2.90 (d, 2H), 1.60 (s, 9H).

Step 3: Preparation of ({4-[(tert butoxy)carbonyl]phenyl}methyl) (η5-2,4-cyclopentadiene-1-yl)] dichlorocyclopentadienyltitanium

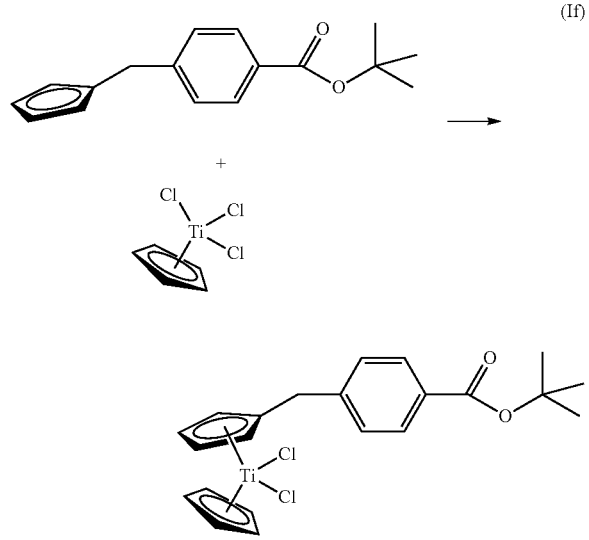

The ester t-butyl 4-(cyclopentadiene-1-ylmethyl)benzoate prepared according to Step 2 above (1.18 mmoles, 300 mg) was dissolved in anhydrous THF (2 ml). The solution was put under static atmosphere of argon and brought to −78° C. A solution of di tert-butyl lithium (1.5 M) in hexane (0.820 ml, 1.23 mmoles, 1.04 eqv) was added very slowly and the resulting solution was kept at −78° C. for 2 h.

A solution of $CpTiCl_3$ (1.18 mmoles, 273 mg, 1 eqv) in THF anhydrous (5 ml) was prepared and brought to −40° C. This solution was added via cannula to the solution previously prepared. The resulting solution was left at room temperature for 3 days.

The mixture was then concentrated and the obtained raw product was dissolved in acetate. The precipitate was filtered. It was the desired product.

$^1$H-NMR (200 MHz): δ 7.98 (d, 2H), 7.25 (d, 2H), 6.51-6.30 (m, 9H), 4.20 (s, 2H), 2.98-2.90 (d, 2H), 1.59 (s, 9H).

Step 4: Preparation of ({4-[(tert butoxy)carbonyl]phenyl}methyl) (η5-2,4-cyclopentadiene-1-yl)]1,2-benzendithiolate cyclopentadienyltitanium

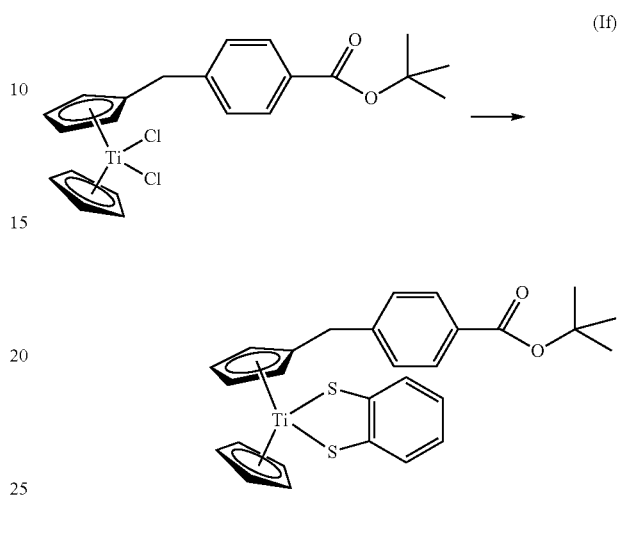

The titanocene dichloride complex obtained from Step 3 above (95 mg, 0.1559 mmoles) was dissolved in anhydrous THF (2 ml) and put under static atmosphere of argon. Anhydrous triethylamine (46.2 μL, 0.334 mmoles, 2.1 eqv) was added, then 21 μL at (0.175 mmoles, 1.1 eqv) of 1,2-dithiobenzene were added. The mixture was kept at room temperature for 12 h. The mixture was then concentrated at reduced pressure and the raw product was purified on a silica gel column by using an eluent mixture of hexane-AcOEt (8:2). A green solid was obtained. It was the compound of Formula (If).

$^1$H-NMR (200 MHz): δ 7.98 (d, 2H), 7.50 (d, 2H), 7.15 (m, 4H), 5.98-5.80 (m, 9H), 3.90 (s, 2H), 1.59 (s, 9H), 1.55 (s, 9H).

Example 2

Step 3: Synthesis of ({[4-(tert-butoxycarbonyl)phenyl]methyl}cyclopentadienyl) dichloro(pentamethylcyclopentadienyl)titanium Step 1 and 2 were performed as in Example 1. Step 3 was performed in the following way:

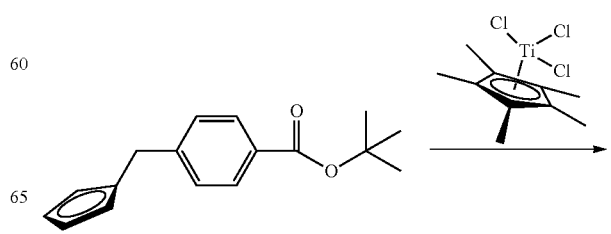

-continued

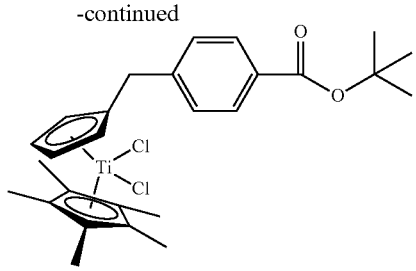

To a solution of tert-butyl 4-(cyclopenta-2,4-dien-1-ylmethyl)benzoate (5 mmol, 0.5M) was added slowly under dry Argon at −78° C. tert-buLi (1.04 eq.) The orange red solution was kept for 2 hours at that temperature. Then a freshly prepared solution of Cp*TiCl₃, namely of the pentamethyl substituted Cp, (0.15M in THF, 1.04 eq. of −40° C.) was added keeping the reaction mixture at T<−70° C. The reaction mixture was allowed to warm up to room temperature and kept for three days. It was evaporated in vacuo and purified by chromatography on silica using Hexane-AcOEt 8-2 Rf=0.32. The product appeared as brown spot on the Tlc.

¹H-NMR CDCl₃ (200 MHz): δ 7.90 (d, 2H), 7.23 (m, 2H), 6.08 (m, 2H), 5.98 (m, 2H), 4.12 (s, 2H), 2.06 (s, 15H), 1.58 (s, 9H).

Step 4: ({[4-(tert-butoxycarbonyl)phenyl]methyl}cyclopentadienyl)benzenedithiolate (pentamethylcyclopentadienyl)titanium The reaction was performed as described in Example 1, step 4, starting from ({[4-(tert-butoxycarbonyl)phenyl]methyl}cyclopentadienyl)dichloro(pentamethylcyclopentadienyl)titanium; i.e. reaction of the alkylated titanocene dichloride with benzenedithiol.

¹H-NMR CDCl₃ (200 MHz): δ 7.78 (d, 2H), 7.34-7.47 (m, 2H), 7.06-7.13 (m, 4H), 5.63 (t, 2H), 5.22 (t, 2H), 3.56 (s, 2H), 2.06 (s, 15H), 1.56 (s, 9H)

Example 3

Deprotection of Compounds

The following examples show method to deprotect the linker moiety L to allow the reaction with the recognition element A.

Example 3a

De-Protection of t-butyl ester to Obtain the Corresponding Acid 2 equivalents of anisole were added to a 0.05 M solution of the titanocene complex obtained from Example 1, step 4, in anhydrous dichloromethane. The solution was brought to 0° C. and TFA was added (20% with respect to DCM). The color of the solution changed suddenly from green to red-orange. The solution was kept at 5° C. for 18 h. The solvent was then removed at a reduced pressure, making sure that all excess TFA was removed. A brown oil was obtained. The residue was treated with THF, then 1.1 equivalents of triethylamine were added. Subsequently 1 equivalent of 1,2 dithiobenzene was added. The solution became suddenly dark and was kept under stirring for 2-3 h. The solvent was removed and the product was purified on a chromatographic column using pure DCM as eluent, then a mixture DCM-MeOH 9-1.

green red green

Example 3b

De-Protection of t-butyl Ester to Obtain the Corresponding Acid 5 equivalents of 1,2-dithiobenzene were added to a 0.05 M solution of the titanocene complex obtained from Example 1, step 4, in anhydrous dichloromethane. The solution was brought to 0° C. and TFA was added (20% with respect to DCM). The color of the solution changed suddenly from green to red-orange. The solution was kept at 5° C. for 18 h. The solvent was then removed at a reduced pressure. A brown oil was obtained. Upon addition of DCM the color changed to green. The formation of the corresponding acid was detected in TLC hexane-ethyl acetate 7:3. The solution was dried and the product was purified on a chromatographic column using pure DCM as eluent, then a mixture DCM-MeOH 9-1. The compound of Formula (1) deprotected was obtained.

$^1$H-NMR CDCl$_3$ (200 MHz): δ 8.03 (d, 2H), 7.57-7.6) (m, 2H), 7.32 (d, 2H), 7.14-7.21 (m, 2H), 5.75-6.07 (2m, 9H), 3.96 (s, 2H)

Example 4

Preparation of a Conjugate of Formula (II) and its Precursors

Attachment of a Targeting Molecule A to the Linker Group L of the Metallocene Complex.

General Procedure for the Conjugation when A is an Aminoacid (see Inorganic Chemistry Communications 8, 2005, 429-432)

1.4 equivalents or DCC (dicyclohexylcarbodiimide) and 1.4 equivalents of HOBTz (3H-[1,2,3]triazolo[4,5-b]pyridin-3-ol) were added under a static atmosphere of argon to a 0.03M solution or the metallocene complex in acid form (1 mmol) obtained from Example 3a above.

Example 4a

[(4-{[(2S)-1-methoxy-1-oxo-3-phenylpropan-2-yl]carbamoyl}phenyl)methyl]}(η5-cyclopentadienyl))1,2-benzendithiolato cyclopentadienyltitanium

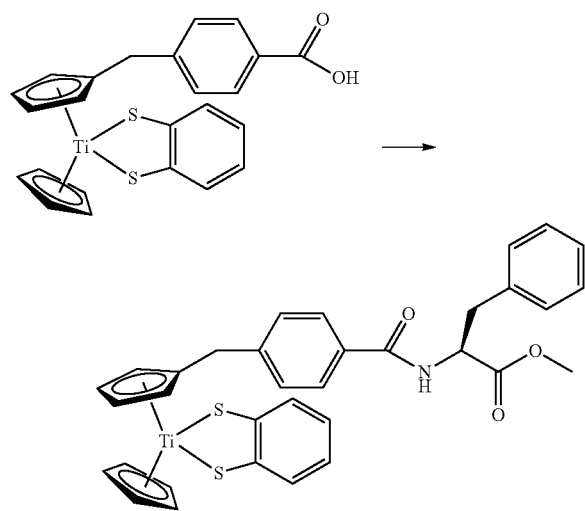

The reaction was performed according to the general procedure using phenylalanine hydrochloride as aminoacid. After the TLC (DCM-MeOH (9:1)) or the reaction mixture indicated complete conversion, the reaction mixture was evaporated to dryness under reduced pressure. The crude product was chromatographed on silica using DCM-AcOEt 10:9:1 (v/v/v) $^1$H-NMR CDCl$_3$ (200 MHz): δ 7.64 (d, 2H), 7.51 (m, 2H), 7.18 (m, 5H), 7.11-7.25 (m, 4H), 6.53 (d, 1H), 6.0 (m, 7H), 5.58 (m, 2H), 5.07 (q, 1H), 3.91 (s, 2H), 3.81 (s, 3H), 3.26 (m, 2H) MS: ε$_z$ 637 (M+Na)$^+$

Example 4b ({[4-({[(1-methoxy-1-oxo-3-phenylpropan-2-yl)carbamoyl]methyl}carbamoyl)phenyl]methyl} (η5-cyclopentadienyl))1,2-benzendithiolato cyclopentadienyltitanium Titanocene-Peptide Conjugation

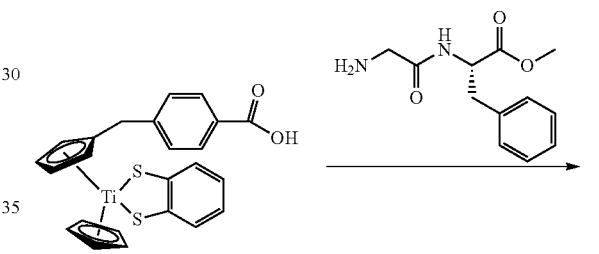

To a solution of ({4-hydroxycarbonyl]phenyl}methyl)(η5-2,4-cyclopentadiene-1-yl)] 1,2-benzendithiolato cyclopentadienyltitanium (0.03M) in DCM was added at 0° C. under inert atmosphere (N$_2$), glcinylbenzlalanine methylester (1.6 eqv), HOBt (hydroxybenzotriazole) (1.5 eqv) e EDCI[1-(3-Dimethylaminopropyl)-3-ethylcarbodiimide HCl (1.56 eqv). The reaction mixture was allowed to come to room temperature and was allowed to stir for 3 hours. Tlc-analysis of the reaction mixture (TLC DCM-AcOEt 9:1, v/v) indicated complete conversion. The reaction mixture was evaporated to dryness in vacuo and subsequently chromatographed on silica gel 60 (eluent DCM-AcOEt 9:1, v/v), Rf=0.34). The product was characterized further by NMR: ({[4-({[(1-methoxy-1-oxo-3-phenylpropan-2-yl)carbamoyl]methyl{carbamoyl)phenyl]methyl}(η5-cyclopentadienyl))1,2-benzendithiolato cyclopentadienyltitanium ¹H-NMR CDCl₃ (200 MHz): δ 7.75 (d, 2H), 7.53 (m, 2H), 7.28-7.06 (m, 9H), 7.00 (t, 1H), 6.63 (d, 1H), 6.06-5.85 (m, 9H), 4.81 (q, 1H), 4.13 (d, 2H), 3.91 (s, 2H), 3.75 (s, 3H), 3.13 (m, 2H).

Esempio 4c

Preparation of Complex [4-({η⁵-[2-η⁵(cyclopentadi-enyl)benzo[d]1,3-dithia-2-titanacyclopentan-2-yl]cyclopentadienyl}methyl)phenyl]({[(diphenylphosphanyl)methyl]sulfanyl})methanone Borano (Formula Ia)

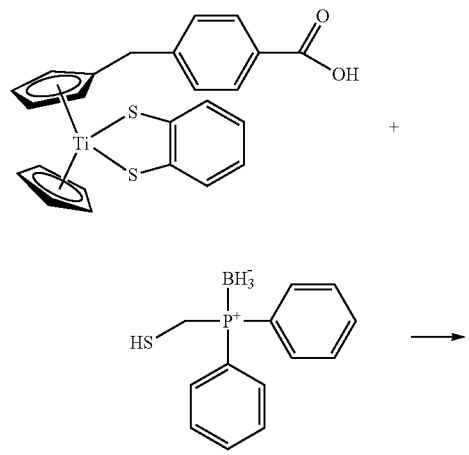

1.4 equivalents of dicyclohexyl carbodiimide (DCC) and dimethylaminopyridine (DMAP) in catalytic amount were added under a static atmosphere of argon to a 0.03M solution in dichloromethane of the metallocene complex in acid form (1 mmol) obtained from Example 3a above and of the diphenylphosphanylmethanol borane complex (1 mmol). The mixture was brought to 0° C.

Triethylamine (0.002 equivalents) and the borano complex of (diphenylphosphanyl)methanethiol were added. After having kept the mixture for 24 h at room temperature it was dried. The crude product was chromatographed with hexane/ethylacetate (7:3 V/V). The result was TLC: Rf: 0.35, MS: ∈_z 703 (M+Na)⁺, 689 (M-BH₃+Na)⁺.

Example 4d

Preparation of the Titanocenyl NHS-ester for Conjugation with Aliphatic Primary Amines

[(4-{[(2,5-dioxopyrrolidin-1-yl)oxy]carbonyl}phenyl)methyl] (η5-cyclopentadienyl)] 1,2-benzendithiolato cyclopentadienyltitanium

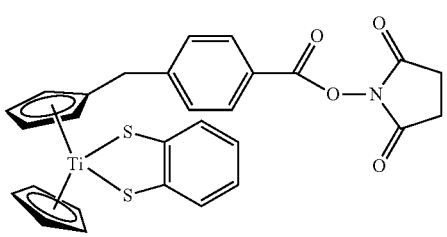

Operating conditions: anhydrous ambient, inert atmosphere.

1.1 equivalents of DCC (Dicyclohexylcarbodide) and 1.1 equivalents of N-hydrosuccinimde were added to a 0.1M solution in dichloromethane or the metallocene complex in acid form obtained from Example 3a above. The mixture was kept at room temperature overnight. Then it was dried and the product was purified on a chromatographic column by using as diluent DCM-AcOEt 98-2 (Rf=0.37). The product was green.

Example 4e

Preparation of the Titanocene Propargylamine Derivative ({4-[(prop-2-yn-1-yl)carbamoyl]phenyl}methyl)(η5-cyclopentadienyl)] 1,2-benzendithiolato cyclopentadienyl titanium

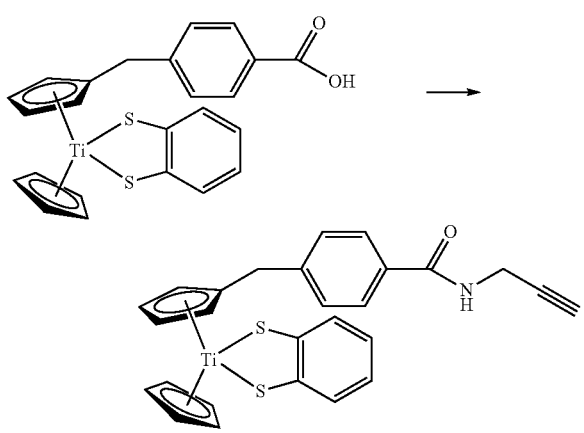

Operating conditions: anhydrous ambient, inert atmosphere.

A 0.03 solution in dry dichloromethane of the metallocene complex in acid form obtained from Example 3a (1 eqv, MW=452) was brought to 0° C. At such temperature propargylamine was added (1.6 eqv, MW=55.08). Then 1-hydroxybenzotriazole (HOBt, 1.5 eqv, MW=135.13) and N-(3-dimethylaminopropyl)-N-ethylcarbodiimide chlorhydrate (EDCT, 1.56 eqv, MW=191.71) were added. The mixture is allowed to reach the room temperature spontaneously and is kept under stirring for about 4 h. The reaction is monitored via TLC (DCM-AcOEt 9:1 Rf=0.52, green spot). When the reaction is completed the mixture is dried and the crude reaction product is purified via a chromatographic column with DCM-AcOEt 95:5 as eluent.

$^1$H-NMR CDCl$_3$ (200 MHz): δ 7.73 (d, 2H), 7.5 (m, 2H), 7.14-7.26 (m, 4H), 6.35 (t (broad) 1H)), 6.0 (m, 7H), 5.76 (m, 2H), 4.26 (m, 2H) 3.88 (s, 2H), 2.26 (t, 1H).

Example 4f

Titanocene-Octreotide Conjugation

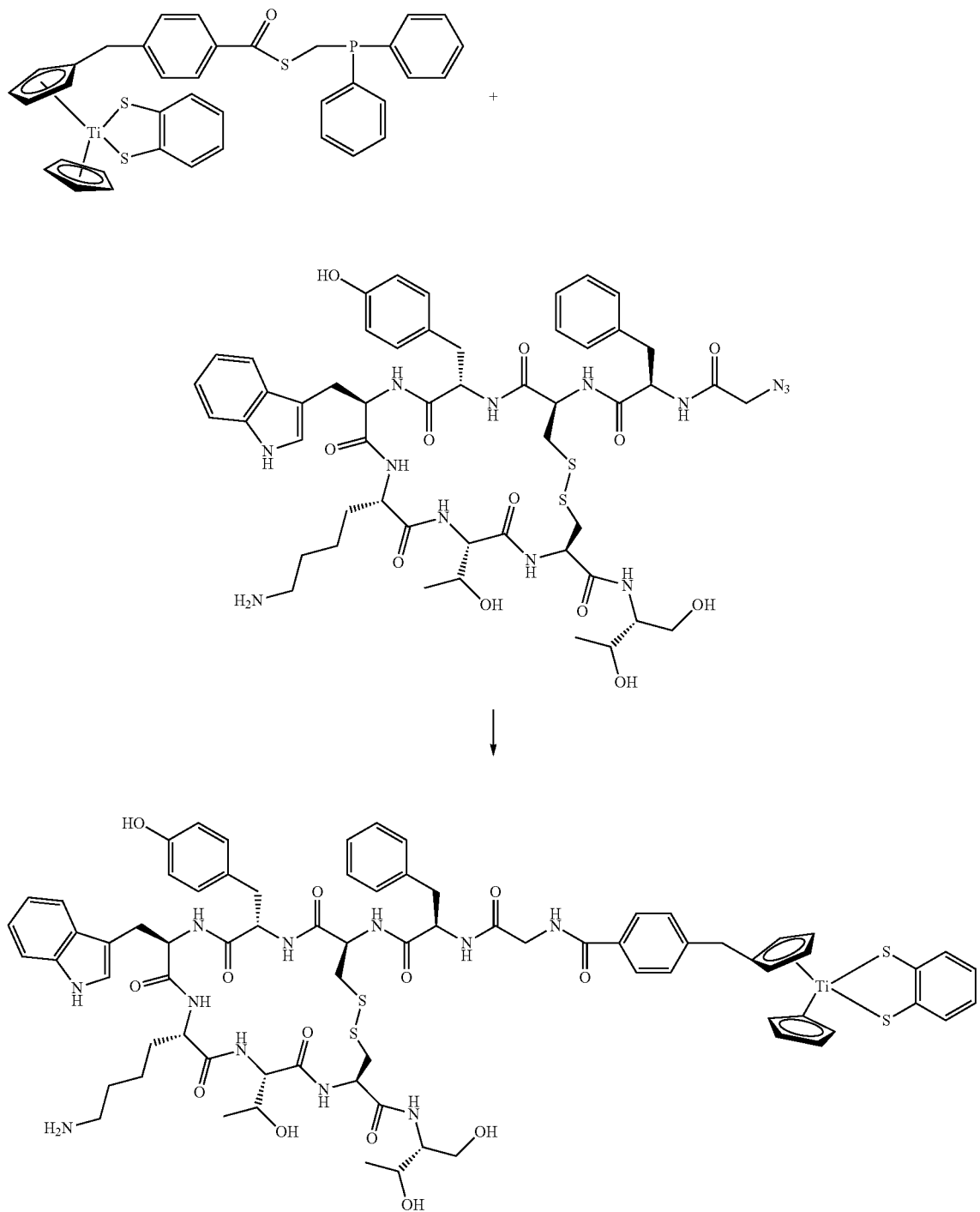

Operating conditions: anhydrous ambient, inert atmosphere.

1 equivalent of octreotide azido-derivative (MW=1102) were added to a 0.045M solution in dry DMF (dimethyl formanide) of the metallocene complex obtained from Example 4c above. (1 eqv, MW=666). The mixture was kept under nitrogen overnight. A sample amount was injected directly into the Mass spectrometer, which revealed a mass of $\epsilon_z$:1238 (M+1)

Example 5

Preparation of Labeled Conjugate of Formula (III)

The following examples show groups $X^1$ and $X^2$ of Formula (II) which can be displaced by a radionuclide $Y^1$ and $Y^2$, e.g. fluoride to produce labeled conjugates of Formula (III)

Example 5a

General Procedure to Replace Cl with Benzoyl

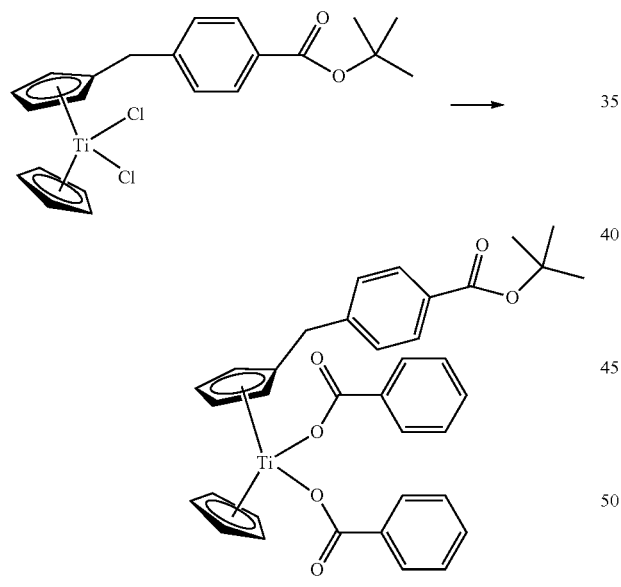

To a solution of the ({4-[(tert-butoxy)carbonyl]phenyl}methyl) titanocene dichloride derivative (95 mg, 0.1559 mmoles) in CHCl₃ (15 ml) it was added distilled water (15 ml). Solid sodium benzoate (2 equivalents) was then added and the biphasic mixture was vigorously stirred for 2 h at room temperature. The organic phase changes from dark red to yellow (S=NaOBz). The mixture was then transferred into a separation funnel, the organic phase was collected and washed with demineralized water (3×3 ml). Chloroform was removed at reduced pressure and the solid obtained had an excellent degree of purity (>95% ¹H NMR).

({4-[(tert-butoxy)carbonyl]phenyl}methyl)titanocene dibenzoate

Example 5b

Procedure to Replace Cl with 4-nitromercaptophenyl

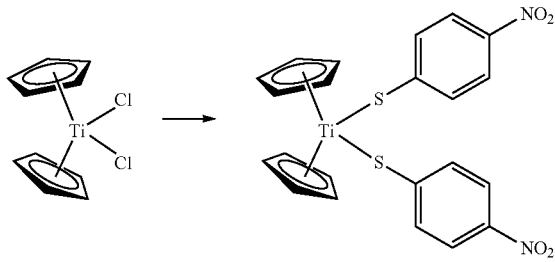

To a solution of bis-cyclopentadienyl titanium dichloride (95 mg, 0.1559 mmoles) in anhydrous toluene (5 ml) it was added p-nitrothiophenol (2 equivalents) under static atmosphere of argon at 25° C. Freshly distilled NEt₃ (2 equivalents) was then added dropwise. The color changed from dark red to brilliant red. The reaction was continued for 18 hours at room temperature. The solvent was removed at reduced pressure and the residue obtained on a silica gel column (RF=0.32; 7/3 Hexane-Ethyl Acetate).

Example 5c

Procedure to Replace Cl with 2-mercaptopiridyl

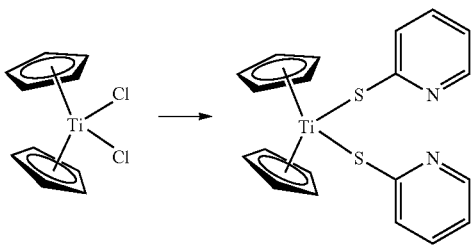

To a solution of bis-cyclopentadienyl titanium dichloride (95 mg, 0.1559 mmoles) in anhydrous toluene (8 ml) it was added 2-mercaptopiridine (2 equivalents) under static atmosphere of argon at 25° C. Freshly distilled NEt₃ (2 equivalents) was then added dropwise. The color changed from dark red to very intense brilliant red. The reaction was continued for 18 hours at room temperature. The product was then centrifuged and the toluene was removed. After 3 washings with 8 ml of toluene the solid was dried under high vacuum for 6 h.

Bis 2-azabenzenethiolatotitanocene

Example 6

Flouridation of a Titanocene-Dipeptide Conjugate

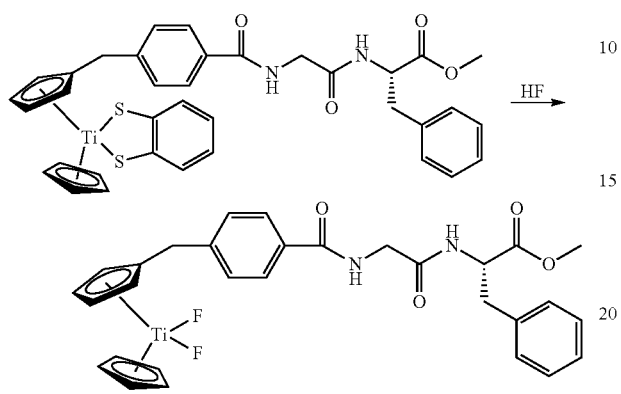

5 equivalents of HF (48%) were added to a solution of benzenedithiolato titanocene glycinylalanylmethylester in McCN (acetonitrile)(0.03M). Within 15-20 min the reaction mixture turned from green to yellow. $CuF_2$ (1 eq.) and MeCN (1 mL) were added to bind the replaced benzenedithiolate. The reaction mixture turned dark and was filtered rapidly through Celite. The filtrate was evaporated to dryness in vacuo. The dark solid was suspended in MeCN and filtered through a column of a PORAPAK RXN RP. The dark material remained on the top of the column while a yellow substance eluted. MS indicates the pure desired product. MS: $\epsilon_z$ 591 $(M+Na)^+$, 1159 $(2M+Na)^-$.

Since the nature of fluoro isotope has no impact on its chemical reactivity, Example 6 above was carried out with $^{19}F$.

Example 7

Preparation of a Conjugate of Formula II and its Precursors

Step 1

Synthesis of 8,8-dibromobicyclo[5.1.0]octane

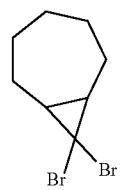

Chemical Formula: $C_8H_{12}Br_2$
Exact Mass: 265.93

To a magnetically stirred solution of cycloheptene (500 mg, 5.20 mmol, 1 eq) in dry Pentane (52 ml) under Ar atmosphere, tBuOK (671 mg, 5.98 mmol, 1.15 eq) was added. Suspension was cooled to 0° C. and $CHBr_3$ (466 µl, 5.20 mmol, 1 eq) was added in a time period of six hours. Then the solution was warmed to Room Temperature (RT) and the resulting dark-brown solution was stirred overnight at RT. Reaction was controlled by TLC (Hexane as eluent) and was quenched with water (10 ml) and concentrated HCl until neutralization. Layers were separated and the aqueous layer was extracted with pentane (3×50 ml). Combined organic phases were dried over $Na_2SO_4$, filtered and concentrated under vacuum to obtain product 8,8-dibromobicyclo[5.1.0] octane as a brown oil that was used for the next step without further purification.

$^1$H-NMR (200 MHz): δ 1.25 (m, 4H); δ 1.75 (m, 4H); δ 2.20 (m, 2H)

Step 2

Synthesis of 6-{[(2E)-2-bromocyclooct-2-en-1-yl]oxy}hexan-1-ol

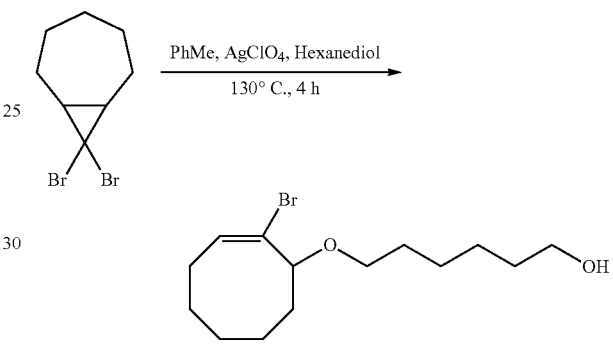

To a magnetically stirred solution of 8,8-dibromobicyclo [5.1.0]octane 650 mg (2.43 mmol, 1 eq) in dry toluene (3 ml) under Ar atmosphere, pyridine (1.75 ml) was added and the flask was covered by an aluminum foil. 1.6 Hexandiol 8602 mg (73 mmol, 30 eq) and $AgClO_4$ 1516 mg (7.29 mmol, 3 eq) were added. The solution was warmed to reflux for 4 h. After this time reaction was cooled to RT and filtered on a celite Pad to remove insoluble Silver salts. To the solution, Brine (20 ml) and $Et_2O$ (40 ml) were added and layers were separated, the aqueous layer was extracted with $Et_2O$ (3×40 ml). Combined organic layers were dried over $Na_2SO_4$ filtered and concentrated under vacuum to obtain 6-{[(2E)-2-bromocyclooct-2-en-1-yl]oxy}hexan-1-ol that was used for the next step without further purification.

MS: $\epsilon_z$ $(M+Na)^+$: 327.19 (isotope pattern indicated one bromine atom).

$^1$H-NMR (200 MHz): δ 6.10 (d, d, 1H); δ 3.80 (m, 1H); δ 3.45 (t, 2H); δ 2.64 (m, 1H); δ 2.10 (m, 2H); δ 1.60 (m, 14H)

Step 3

Synthesis of 6-(cyclooct-2-yn-1-yloxy)hexan-1-ol

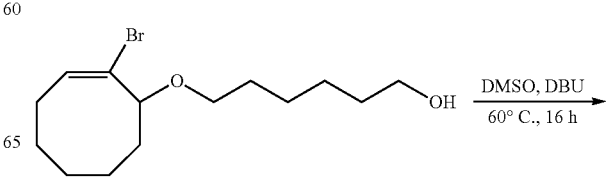

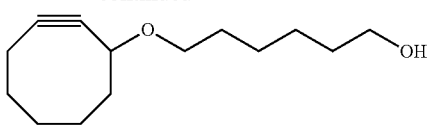

To a magnetically stirred solution of 6-{[(2E)-2-bromocyclooct-2-en-1-yl]oxy}hexan-1-ol 200 mg (0.658 mmol 1 eq) in dry DMSO (3.5 ml) under Ar atmosphere, DBU (6.58 mmol, 10 eq, 1 ml) were added. The reaction was warmed to 60° C. and was stirred at this temperature for 16 h. Reaction was controlled until complete disappearance of the starting material by TLC (Hexane/AcOEt 7/3 as eluent). The reaction was quenched with a saturated solution of $NH_4Cl$, layers were separated and the aqueous layer was extracted with $Et_2O$ (3×20 ml). Combined organic layer was washed with Brine (20 ml), dried over $Na_2SO_4$ filtered and concentrated under vacuum. Raw material was purified by chromatography on silica gel column (55 g) (Hexane:AcOEt 7/3) to obtain 6-(cyclooct-2-yn-1-yloxy)hexan-1-ol.

$^1$H-NMR (200 MHz): δ 4.10 (m, 1H); δ 3.50 (m, 4H); δ 3.12 (m, 1H); δ 1.70 (m, 14H) MS: $\epsilon_z(M+Na)^+$: 247.17 (isotope pattern indicates no bromine atom)

Step 4

Synthesis of 3-[(6-iodohexyl)oxy]cyclooct-1-yne

To a magnetically stirred solution of 6-(cyclooct-2-yn-1-yloxy)hexan-1-ol (126 mg, 0.566 mmol, 1 eq) in dry THF (1.5 ml) under Ar atmosphere, Imidazole (1.1 eq, 0.622 mmol, 42 mg) and $Ph_3P$ (1.3 eq, 0.736 mmol, 193 mg) were added. The solution was cooled to 0° C. and Iodine (0.680 mmol, 1.2 eq, 173 mg) was added in three portions. Solution was warmed to RT and stirred for 4 h. The reaction was monitored by TLC (hexane 100% as eluent), quenched by addition of a saturated solution of $Na_2SO_3$ (3 ml) and the phases were separated. The aqueous phase was extracted with $Et_2O$ and combined organic layers were dried over $Na_2SO_4$, filtered and concentrated under vacuum. The obtained raw product was purified using a column of silica gel (40 g) and Hexane as eluent to obtain 3-[(6-iodohexyl)oxy]cyclooct-1-yne.

$^1$H-NMR (200 MHz): δ 4.10 (m, 1H); δ 3.50 (m, 1H); δ 3.25 (m, 3H); δ 1.75 (m, 20H)

Step 5

Synthesis of 3-{[6-cyclopentadienyl]hexyl}oxy}cycloocty-1-yne

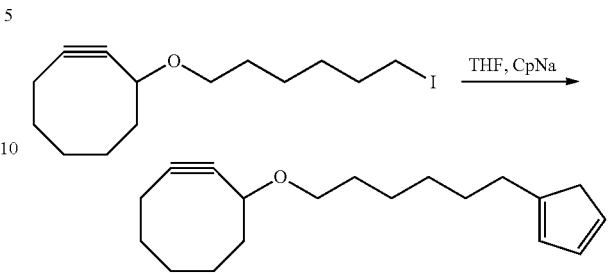

To a magnetically stirred solution of 3-[(6-iodohexyl)oxy]cyclooct-1-yne (36 mg, 0.105 mmol, 1 eq) in dry THF (0.3 ml) under Ar atmosphere, DMPU was added (25 µl, 0.210 mmol, 2 eq). The reaction was cooled to −78° C., and then a solution of CpNa (55 µl, 0.105 mmol, 1 eq) in dry THF (0.200 ml) was added dropwise. The reaction was completed in 2 h and the reaction was quenched by the addition of a saturated solution of $NH_4Cl$ (1 ml), Water (1 ml) and MTBE (3 ml) and layers were separated. The aqueous layer was extracted with MTBE (3×10 ml). Combined organic layers were dried over $Na_2SO_4$ filtered and concentrated under vacuum. The residue was purified by a column of silica gel (10 g) using Hexane as eluent to obtain 3-{[6-cyclopentadienyl]hexyl}oxy}cycloocty-1-yne.

$^1$H-NMR-(200 MHz): δ 6.05 (m, 4H); δ 4.08 (m, 1H); δ 3.40 (m, 2H); δ 2.65 (t, 2H); δ 1.8 (m, 20H)

Step 6

Synthesis of Dichloro({3-[6-(cyclooct-2-yn-1-yloxy)hexyl]cyclopenta-dienyl}) (pentamethyl cyclopentadienyl) titanium (Compound Ig)

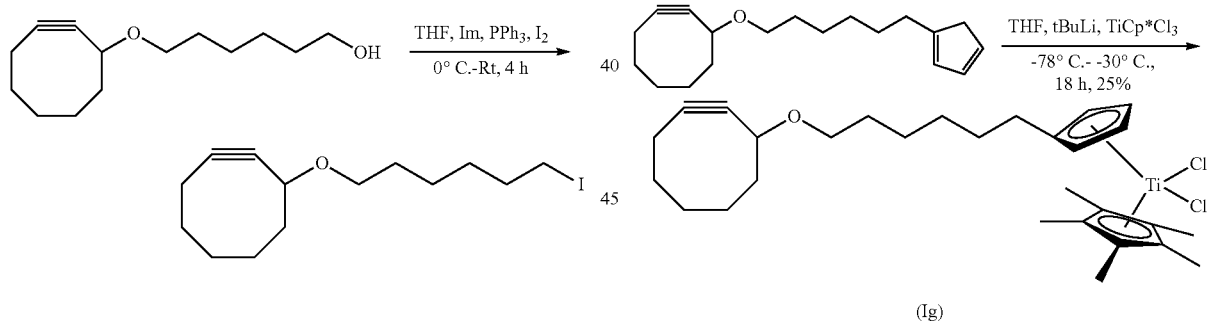

Magnetically stirred solution of 3-{[6-cyclopentadienyl]hexyl}oxy}cycloocty-1-yne (31 mg, 0.123 mmol, 1 eq) in dry THF (0.4 ml) under Ar atmosphere was cooled to −78° C. and then tBuLi (solution 1.7M in pentane, 69 µl, 1.05 eq) was added slowly and the resulting yellow solution was stirred for 1 h at −78° C. Then a solution of CP*TiCl$_3$, namely of the pentamethyl substituted Cp, (28 mg, 0.098 mmol, 0.8 eq) was added dropwise. The reaction was controlled by TLC (Hexane/AcOEt, 85/15 as eluent). After 2 h the reaction was warmed to −30° C. and was stirred at this temperature overnight. After this time the reaction was concentrated under vacuum and the residue was purified on a column of silica gel (10 g) using Hexane/AcOEt 85/15 as eluent, to obtain Dichloro({3-[6-(cyclooct-2-yn-1-yloxy)hexyl]cyclopentadienyl}) (pentamethyl cyclopentadienyl)titanium.

$^1$H-NMR-(200 MHz): δ 6.10 (m, 1H); δ 4.10 (m, 1H); δ 3.40 (m, 2H); δ 2.60 (t, 2H); δ 1.8 (m, 34H)

MS: $\epsilon_z (M+Na)^+$: 548.25

Step 7

Conjugation of dichloro({3-[6-(cyclooct-2-yn-1-yloxy)hexyl]cyclopenta-dienyl}) (pentamethyl cyclopentadienyl)titanium with Octreotide Bearing a azidoacetyl Group

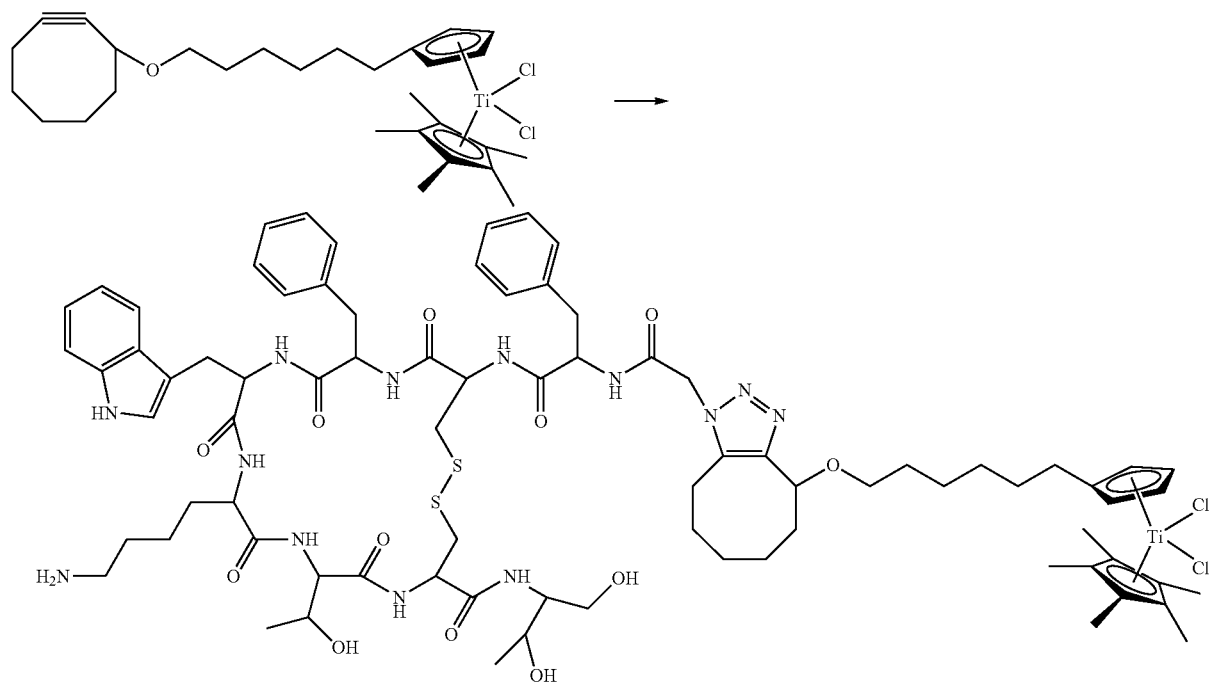

Operating conditions: anhydrous ambient, inert atmosphere.

1 equivalent of octreotide azido-derivate (MW=1102) were added to a 0.045M solution in dry DMF (dimethylformamide) of the metallocene complex dichloro({3-[6-(cyclooct-2-yn-1-yloxy)hexyl]cyclopenta-dienyl}) (pentamethyl cyclopentadienyl) titanium (1 eqv, MW=547). The mixture was kept under nitrogen overnight. A sample amount was injected directly into the Mass spectrometer, which revealed a mass of $\epsilon_z(M+H)^+$: 1626.42.

Step 8

Fluoridation of Titanocene-Octreotide Conjugate

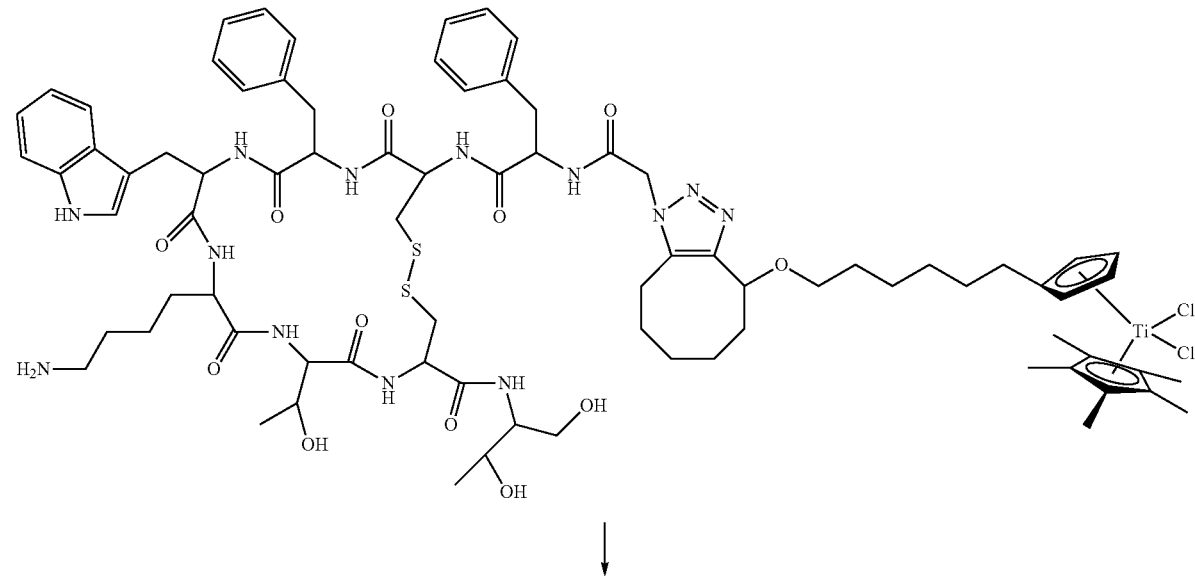

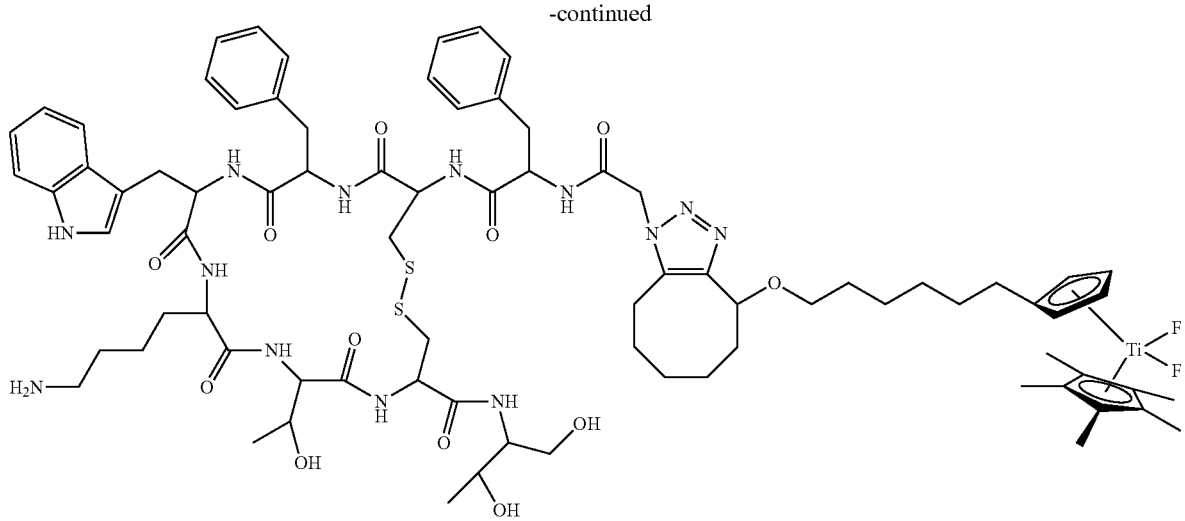

To a magnetically stirred solution of titanocene-octreotide conjugate synthesized in step 7 (1 eq) in a mixture of water (0.2 ml) and CHCl$_3$ (0.200 ml), KF (2.5 mg, 0.040 mmol, 2.2 eq) was added. After 20 h the Cl—F-exchange was complete. The solution was filtered and the residue was concentrated under vacuum.

MS: $\epsilon_z$(M+H)$^+$: 1594.

What is claimed is:

1. Metallocene compound of general formula (I):

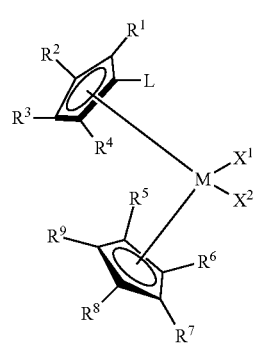

Formula I wherein:
M is a metal selected from the group consisting of titanium, zirconium and hafnium;
X$^1$ and X$^2$, which can be the same or different, are a halogen atom, a R', OR', OCOR', SR', NR'$_2$ or PR'$_2$ group, wherein the R' substituents are linear or branched, saturated or unsaturated C$_1$-C$_{20}$ alkyl, C$_3$-C$_{20}$ cycloalkyl, C$_6$-C$_{20}$ aryl, C$_7$-C$_{20}$ alkylaryl, C$_7$-C$_{20}$ arylalkyl radicals, optionally containing one or more heteroatoms belonging to the groups 13-17 of the Periodic Table of the Elements;
X$^1$ and X$^2$ can also be interconnected via a cyclic structure of <40 atoms comprising one or more of C, N, O, F, Si, B, P;
R$^1$, R$^2$, R$^3$, R$^4$, R$^5$, R$^6$, R$^7$, R$^8$ and R$^9$, the same or different, are H or linear or branched, saturated or unsaturated C$_1$-C$_{20}$ alkyl, C$_3$-C$_{20}$ cycloalkyl, C$_6$-C$_{20}$ aryl, C$_7$-C$_{20}$ alkylaryl, C$_7$-C$_{20}$ arylalkyl radicals, optionally containing one or more heteroatoms belonging to the groups 13-17 of the Periodic Table of the Elements;
two or more adjacent R$^1$, R$^2$, R$^3$, R$^4$, R$^5$, R$^6$, R$^7$, R$^8$ and R$^9$ groups on a cyclopentadienyl residue may be connected by a saturated or unsaturated bridge containing up to 40 atoms comprising one or more of C, N, S, O, F, Si, B, P, said bridge optionally containing or being part of up to 5 carbo- or hetero-cycles;
L is a linker having a functional end, selected from the group consisting of:

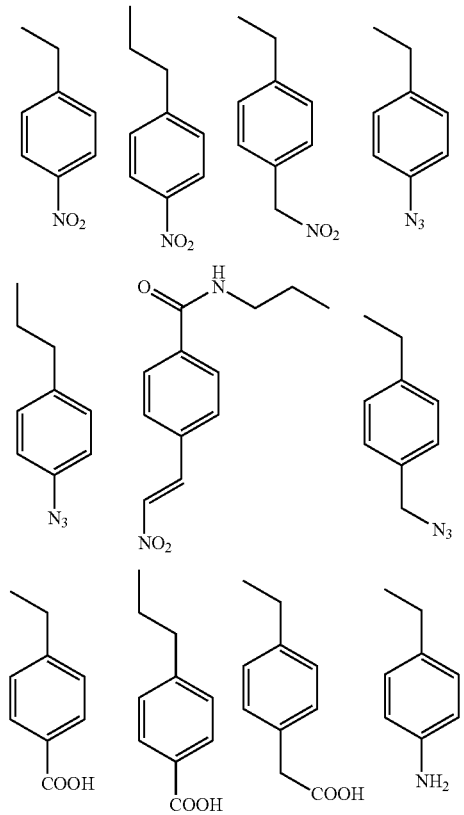

-continued
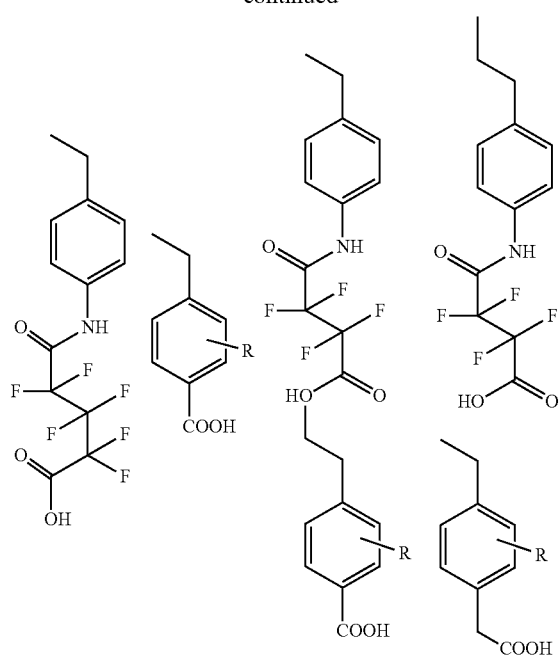
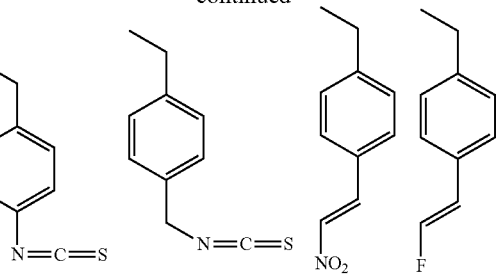
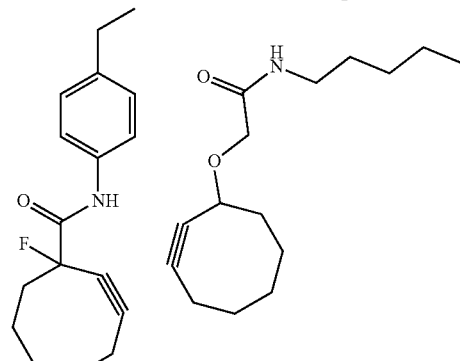
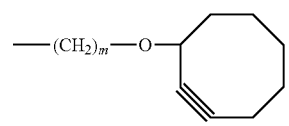
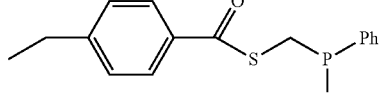
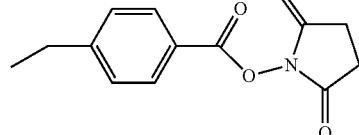
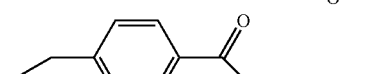
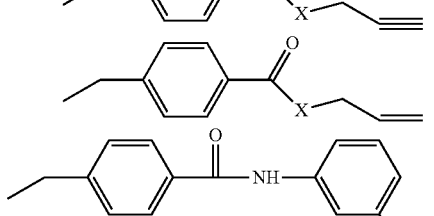
wherein:
Ph=phenyl;
X=R'NH, in which R' is as defined above;
R is selected from the group consisting of F, $CH_2F$, $CHF_2$, $CF_3$, $OCF_3$;
Ar is $C_6$-$C_{20}$ aryl, $C_7$-$C_{20}$ alkylaryl, or $C_7$-$C_{20}$ arylalkyl radical, optionally containing one or more heteroatoms belonging to the groups 13-17 of the Periodic Table of the Elements;

m=2-20;
wherein the functional end of said linker group L is optionally protected.

2. Metallocene compound according to claim 1, wherein M is titanium.

3. Metallocene compound according to claim 1, wherein the substituents $R^1$, $R^2$, $R^3$, $R^4$, $R^5$, $R^6$, $R^7$, $R^8$, $R^9$, which can be the same or different, are selected from the group consisting of H, methyl, benzyl, isobutyl, tert-butyl, methoxy, trimetylsilyl, 1,3-butadiene-1,4-diyl.

4. Metallocene compound according to claim 1, wherein the substituents $R^1$, $R^2$, $R^3$, $R^4$, $R^5$, $R^6$, $R^7$, $R^8$, $R^9$ are H.

5. Metallocene compound according to claim 1, wherein the substituents $X^1$ and $X^2$ are selected from the group consisting of F, Cl, Br, I, alkynes, OR" or SR", wherein R" is a divalent radical selected from the group consisting of $C_6$-$C_{20}$ arylidene being either unsubstituted or substituted with a group comprising 2-40 C, N, O, F, Si, B, P atoms.

6. Metallocene compound according to claim 5, wherein R" is phenylene.

7. Metallocene compound according to claim 1, wherein the linker L has a functional terminal group selected from the group consisting of phosphine, azide, alkene, alkyne, cycloalkyne, carboxylic acid, carboxylic ester, thiol, said functional terminal group being optionally protected.

8. Conjugate of Formula (II):

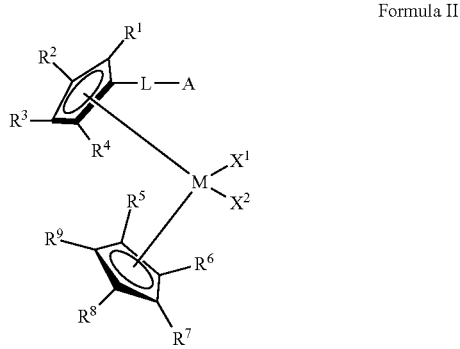

Formula II wherein M, X, $R^1$, $R^2$, $R^3$, $R^4$, $R^5$, $R^6$, $R^7$, $R^8$, $R^9$ and L are as defined in claim 1; and
A is a targeting molecule selected from the group consisting of oligonucleotides, hormones, growth factors, cytokines, chemokines, angiogenic factors, anti-angiogenic factors, immunomodulators, peptides, polypeptides, proteins, nucleic acids, antibodies, antibody fragments, drugs, interleukins, interferons, oligosaccharides, polysaccharides, lipids, cell receptor-binding agents, siderophores and vitamins.

9. Conjugate according to claim 8, wherein the linker L is conjugated to the molecule A via a terminal group selected from the group consisting of azide, alkene, alkyne, cycloalkyne; carboxylic acid, carboxylic ester, thiol, and the targeting molecule A is selected from the group consisting of peptides, polypeptides, proteins.

10. Method of preparation of conjugates of Formula (II) according to claim 8 by reacting a metallocene of Formula (I) according to claim 1 with a targeting molecule A selected from the group consisting of oligonucleotides, hormones, growth factors, cytokines, chemokines, angiogenic factors, anti-angiogenic factors, immunomodulators, peptides, polypeptides, proteins, nucleic acids, antibodies, antibody fragments, drugs, interleukins, interferons, oligosaccharides, polysaccharides, lipids, cell receptor-binding agents, siderophores and vitamins.

11. Method according to claim 10 characterized in that said reaction forms a bond selected from the group consisting of amide, ester, anhydride, carbonate, carbamate, dithiocarbamate, ether, thioether, disulfide, urea, thiourea, triazoyl, amine, imine, oxime and hydrazone bonds.

12. Radionuclide labeled conjugate of Formula (III):

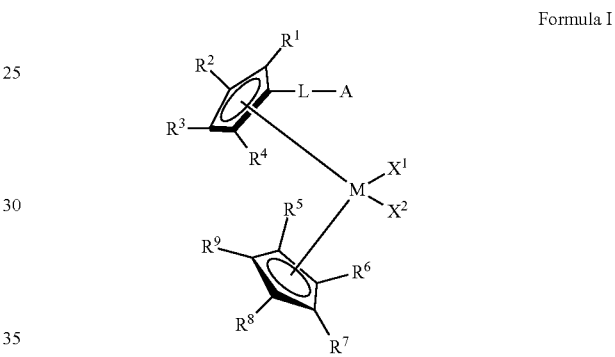

Formula I wherein:
Y is a radionuclide selected from the group consisting of $^{18}F$ and $^{19}F$;
M, $R^1$, $R^2$, $R^3$, $R^4$, $R^5$, $R^6$, $R^7$, $R^8$, $R^9$, L and A are as defined in claim 1.

13. Radionuclide labeled conjugate according to claim 12, wherein A is a targeting molecule selected from the group consisting of oligonucleotides, hormones, growth factors, cytokines, chemokines, angiogenic factors, anti-angiogenic factors, immunomodulators, peptides, polypeptides, proteins, nucleic acids, antibodies, antibody fragments, drugs, interleukins, interferons, oligosaccharides, polysaccharides, lipids, cell receptor-binding agents, siderophores and vitamins.

14. Radionuclide labeled conjugate according to claim 12, wherein Y is $^{18}F$.

* * * * *